(12) United States Patent
DeRosa et al.

(10) Patent No.: US 12,377,053 B2
(45) Date of Patent: Aug. 5, 2025

(54) CATIONIC POLYMERS

(71) Applicant: Translate Bio, Inc., Waltham, MA (US)

(72) Inventors: Frank DeRosa, Waltham, MA (US); Michael Heartlein, Waltham, MA (US); Shrirang Karve, Waltham, MA (US); Zarna Patel, Waltham, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

(21) Appl. No.: 18/625,655

(22) Filed: Apr. 3, 2024

(65) Prior Publication Data
US 2024/0398720 A1   Dec. 5, 2024

Related U.S. Application Data

(62) Division of application No. 16/966,214, filed as application No. PCT/US2019/016291 on Feb. 1, 2019, now Pat. No. 11,975,110.

(60) Provisional application No. 62/625,631, filed on Feb. 2, 2018.

(51) Int. Cl.
| | |
|---|---|
| *C08G 63/685* | (2006.01) |
| *A61K 9/00* | (2006.01) |
| *A61K 9/14* | (2006.01) |
| *A61K 9/51* | (2006.01) |
| *A61K 38/17* | (2006.01) |
| *A61K 38/45* | (2006.01) |
| *A61K 48/00* | (2006.01) |
| *C07D 319/12* | (2006.01) |
| *C08G 63/78* | (2006.01) |
| *C12N 15/113* | (2010.01) |

(52) U.S. Cl.
CPC .......... *A61K 9/5153* (2013.01); *A61K 9/0019* (2013.01); *A61K 9/14* (2013.01); *A61K 9/5123* (2013.01); *A61K 9/5146* (2013.01); *A61K 38/1709* (2013.01); *A61K 38/45* (2013.01); *C07D 319/12* (2013.01); *C08G 63/6852* (2013.01); *C08G 63/78* (2013.01); *C12Y 201/03003* (2013.01); *C12N 15/113* (2013.01); *C12N 2310/14* (2013.01); *C12N 2310/141* (2013.01); *C12N 2320/32* (2013.01)

(58) Field of Classification Search
None
See application file for complete search history.

(56) References Cited

U.S. PATENT DOCUMENTS

| | | |
|---|---|---|
| 6,517,869 B1 | 2/2003 | Park et al. |
| 2017/0246319 A1 | 8/2017 | Derosa et al. |

FOREIGN PATENT DOCUMENTS

| | | |
|---|---|---|
| WO | WO 2005/077882 A1 | 8/2005 |
| WO | WO 2019/152802 A1 | 8/2019 |

OTHER PUBLICATIONS

Gerhardt et al., Biomacromol., 2006, 7(6), pp. 1735-1742. (Year: 2006).*
Gerhardt et al., "Functional Lactide Monomers: Methodology and Polymerization", Biomacromolecules, May 24, 2006, 7(6): 1735-1742.
International Preliminary Report on Patentability for PCT International Patent Application No. PCT/US2019/016291, dated Jun. 12, 2019.
International Search Report and Written Opinion for PCT International Patent Application No. PCT/US2019/016291, dated Jun. 12, 2019.
Martin-Herranz et al., "Surface Functionalized Cationic Lipid-DNA Complexes for Gene Delivery: PEGylated Lamellar Complexes Exhibit Distinct DNA-DNA Interaction Regimes", Biophysical Journal, Feb. 1, 2004, 86: 1160-1168.
Ward et al., "Systemic circulation of poly(L-lysine)/DNA vectors is influenced by polycation molecular weight and type of DNA: differential circulation in mice and rats and the implications for human gene therapy", Blood, Apr. 15, 2001,97: 2221-2229.

* cited by examiner

*Primary Examiner* — Brian Gulledge
(74) *Attorney, Agent, or Firm* — LATHROP GPM LLP; James H. Velema, Esq.

(57) ABSTRACT

Disclosed are cationic polymers comprising monomers such as those described in Formula (I),

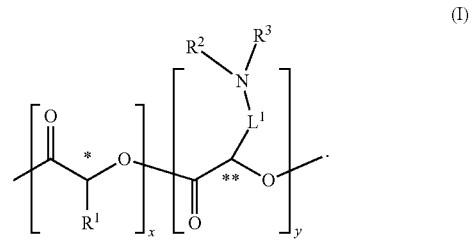

Such polymers can be useful for the preparation of therapeutic compositions (e.g., compositions comprising nucleic acids such as mRNA). Additionally, therapeutic compositions comprising these cationic, biodegradable polymers can have improved properties and reduced toxicity.

20 Claims, No Drawings

Specification includes a Sequence Listing.

CATIONIC POLYMERS

RELATED APPLICATIONS

This application is a divisional of U.S. patent application Ser. No. 16/966,214, filed Jul. 30, 2020, which is a 35 U.S.C. § 371 filing of International Patent Application No. PCT/US2019/016291, filed Feb. 1, 2019, which claims priority to U.S. Provisional Patent Application Ser. No. 62/625,631, filed Feb. 2, 2018, the entire disclosures of which are incorporated herein by reference.

SEQUENCE LISTING

The instant application contains a Sequence Listing which has been submitted electronically in XML format and is hereby incorporated by reference in its entirety. Said XML file, created on Apr. 3, 2024, is named 753679_SA9-851USDIV_ST26.xml and is 7,110 bytes in size.

BACKGROUND

Nucleic acids have been explored as a potential therapeutic option for certain disease states. In particular, ribonucleic acid (RNA) interference (RNAi) using, for example, small interfering RNA (siRNA), short hairpin RNA (shRNA), and antisense RNA (aRNA) approaches have been the subject of significant research and clinical development, for example, for binding to messenger RNA (mRNA), long non-coding RNA (lncRNA), micro-RNA (miRNA) and other endogenous targets. More recently, administration of mRNA, multimeric coding nucleic acid (MCNA), polymeric coding nucleic acid (PCNA), guide RNA (gRNA) and CRISPR RNA (crRNA) have been investigated as possible treatments of various diseases. However, the delivery of nucleic acids as therapeutics remains a challenge.

SUMMARY OF THE INVENTION

The present invention provides, among other things, cationic polymers useful in delivering nucleic acids as a therapeutic. The invention is based, in part, on the surprising discovery that the polymers described herein provide safe and efficient delivery of therapeutic nucleic acids such as mRNA. In particular, the polymers of the present invention may provide one or more advantages over other polymers. For example, as described in more detail herein, the polymers of the present invention may be beneficial in the preparation of dry powder pharmaceutical formulations. Further, the polymers described herein can improve the in vivo delivery of therapeutic nucleic acids such as mRNA. Thus, the polymers of the present invention may provide more potent and/or safer nucleic acid delivery for the treatment of a variety of diseases.

In one aspect, the invention features polymers that comprise monomers having the following structure,

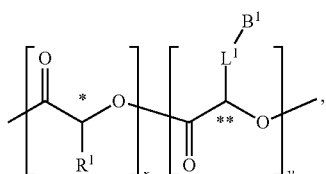

wherein
$R^1$ is $C_6$-$C_{20}$ alkyl, $C_6$-$C_{20}$ alkenyl, or $C_6$-$C_{20}$ alkynyl;
$L^1$ is $C_2$-$C_{20}$ alkylene;
$B^1$ is $NR^2R^3$ or a 5- to 10-membered heteroaryl group;
$R^2$ is hydrogen or $C_1$-$C_{20}$ alkyl;
$R^3$ is hydrogen, $C_1$-$C_{20}$ alkyl, or an N-protecting group;
or $R^2$ and $R^3$, together with the nitrogen to which they are attached, combine to form a 5- to 10-membered heterocyclic group;
x is an integer of 5 to 500; and
y is an integer of 5 to 500.

In a second aspect, the invention features polymers that comprise a repeating unit having the following structure,

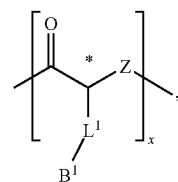

wherein
$L^1$ is $C_2$-$C_{20}$ alkylene;
Z is O or $NR^4$;
$B^1$ is $NR^2R^3$ or a 5- to 10-membered heteroaryl group;
each of $R^2$ and $R^3$ is hydrogen or $C_1$-$C_{20}$ alkyl; or $R^2$ and $R^3$, together with the nitrogen to which they are attached, combine to form a 5- to 10-membered heterocyclic group;
$R^4$ is hydrogen or $C_1$-$C_{20}$ alkyl;
x is an integer of 5 to 1000.

In a third aspect, the invention features a polymer that comprises two different monomers that have the following structure,

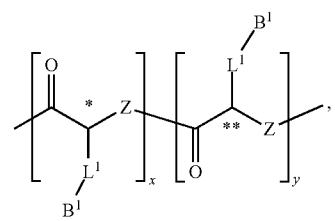

wherein
$L^1$ is $C_2$-$C_{20}$ alkylene;
Z is O or $NR^4$;
$B^1$ is $NR^2R^3$ or a 5- to 10-membered heteroaryl group;
each of $R^2$ and $R^3$ is independently hydrogen or $C_1$-$C_{20}$ alkyl; or $R^2$ and $R^3$, together with the nitrogen to which they are attached, combine to form a 5- to 10-membered heterocyclic group;
$R^4$ is hydrogen or $C_1$-$C_{20}$ alkyl;
x is an integer of 5 to 500;
y is an integer of 5 to 500; and
wherein the two monomers differ in the identity of -$L^1B^1$, Z, or in the stereochemistry of the carbon marked by the single asterisk and the carbon marked by the double asterisk.

In a fourth aspect, the invention features a compound having the following structure,

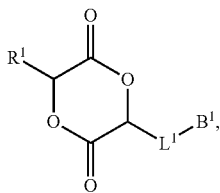

or a salt thereof, wherein
$R^1$ is $C_6$-$C_{20}$ alkyl, $C_6$-$C_{20}$ alkenyl, or $C_6$-$C_{20}$ alkynyl;
$L^1$ is $C_2$-$C_{20}$ alkylene;
$B^1$ is $NR^2R^3$ or a 5- to 10-membered heteroaryl group;
$R^2$ is hydrogen or $C_1$-$C_{20}$ alkyl;
$R^3$ is hydrogen, $C_1$-$C_{20}$ alkyl, or an N-protecting group;
or $R^2$ and $R^3$, together with the nitrogen to which they are attached, combine to form a 5- to 10-membered heterocyclic group.

In some aspects, the present invention provides methods of preparing the polymers as described herein.

In some aspects, the present invention provides a composition (e.g., a pharmaceutical composition) comprising a polymer as described herein and a nucleic acid such as mRNA.

In some aspects, the present invention provides methods of treating a disease in a subject comprising administering to the subject a composition comprising a polymer as described herein and a nucleic acid such as mRNA.

In some aspects, the present invention provides a composition comprising a lipid nanoparticle comprising a polymer as described herein, one or more polynucleotides, and one or more PEG-modified lipids. In embodiments, the composition comprises about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% of one or more PEG-modified lipids. In embodiments, the composition comprises up to about 1%, up to about 2%, up to about 3%, up to about 4%, up to about 5%, up to about 6%, up to about 7%, up to about 8%, up to about 9%, or up to about 10% of one or more PEG-modified lipids. In embodiments, the composition comprises about 7% of one or more PEG modified lipids.

In embodiments, the PEG lipid is a methoxypoly(ethylene glycol) (mPEG) glyceride. In embodiments, the mPEG glyceride lipid is a diacylglycerol-PEG (DMG-PEG) (e.g., DMG-PEG2000, DMG-PEG5000). In embodiments, the mPEG glyceride lipid is a distearoylglycerol-PEG (DSG-PEG) (e.g., DSG-PEG2000, DSG-PEG5000). In embodiments, the DMG-PEG has the structure:

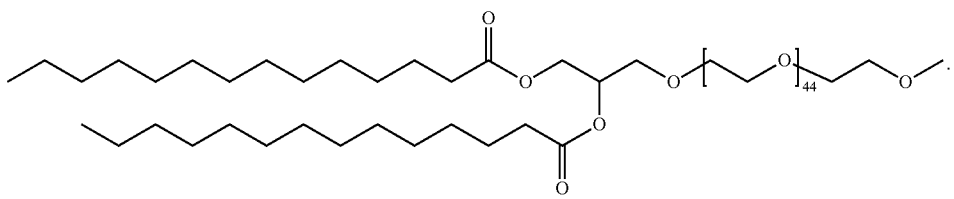

DMG-PEG2000

In embodiments, the DSG-PEG has the structure:

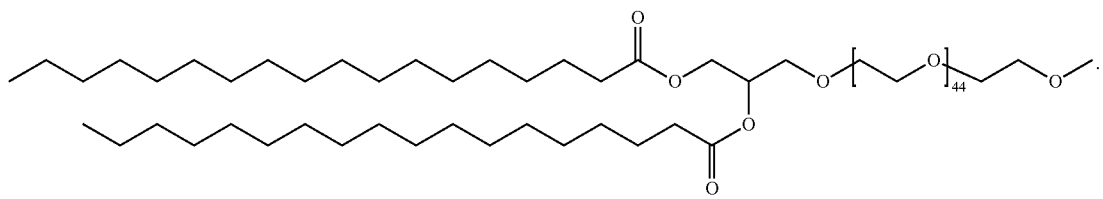

DSG-PEG2000

In embodiments, the PEG lipid is an mPEG ceramide. In embodiments, the mPEG ceramide lipid is $C_8$ PEG ceramide. In embodiments, the mPEG ceramide lipid is $C_{16}$ PEG ceramide. In embodiments, the $C_8$ PEG ceramide has the structure:

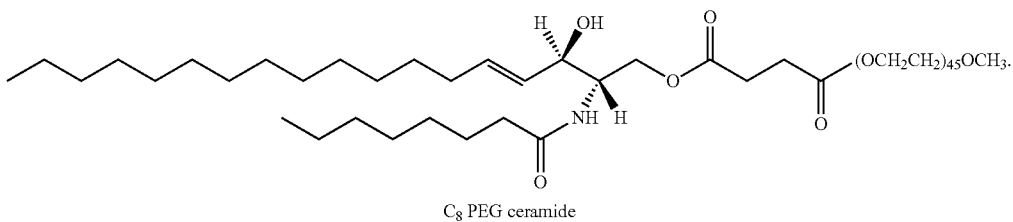

$C_8$ PEG ceramide

In embodiments, the $C_{16}$ PEG ceramide has the structure:

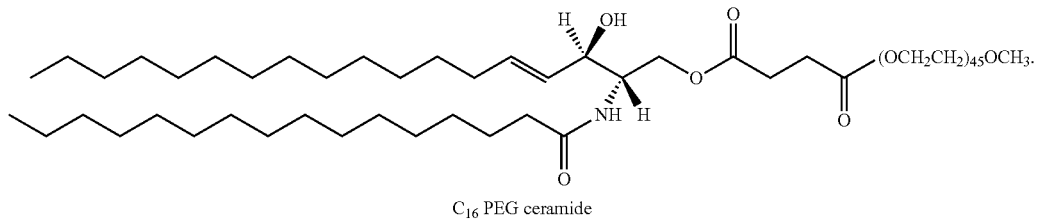

$C_{16}$ PEG ceramide

In embodiments, the PEG lipid is an mPEG phospholipid. In embodiments, the mPEG phospholipid is 1,2-Distearoyl-sn-glycero-3-phosphoethanolamine (DSPE)(18-0)-PEG. In embodiments, the mPEG phospholipid is 1,2-Dioleoyl-sn-Glycero-3-Phosphoethanolamine (DOPE)(18-1)-PEG. In embodiments, the mPEG phospholipid is 1,2-Ditetradecanoyl-sn-glycero-3-phosphoethanolamine (DMPE)(14-0)-PEG. In embodiments, the mPEG phospholipid is DPPE (16-0)-PEG. In embodiments, the DSPE(18-0)-PEG has the following structure:

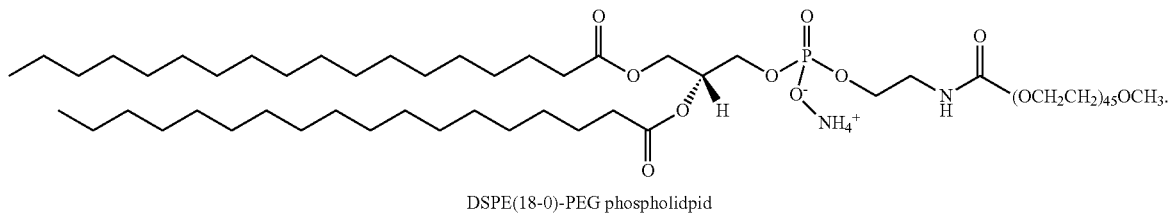

DSPE(18-0)-PEG phospholidpid

In embodiments, the lipid nanoparticle further comprises one or more cationic lipids, one or more non-cationic lipids, and/or one or more cholesterol-based lipids.

In some aspects, the present invention provides methods of treating a disease in a subject comprising administering to the subject a composition comprising a polymer as described herein, a lipid nanoparticle comprising one or more polynucleotides (e.g., mRNA), and one or more PEG-modified lipids. In embodiments, administration of the composition comprises intramuscular administration to the subject. In embodiments administration of the composition comprises intravenous administration to the subject. In certain embodiments, 24 hours after intravenous administration of the composition to the subject, protein expression is observed in the spleen.

In embodiments, the compositions described herein comprise mRNA, which comprises an oligonucleotide sequence that encodes a peptide or protein. In embodiments, the mRNA encodes a peptide or protein for use in the delivery to or treatment of the lung of a subject or a lung cell. In embodiments, the mRNA encodes cystic fibrosis transmembrane conductance regulator (CFTR) protein. In embodiments, the mRNA encodes a peptide or protein for use in the delivery to or treatment of the liver of a subject or a liver cell. In embodiments, the mRNA encodes ornithine transcarbamylase (OTC) protein. In embodiments, the mRNA encodes a peptide or protein for use in a vaccine. In embodiments, the mRNA encodes an antigen.

DETAILED DESCRIPTION OF CERTAIN EMBODIMENTS

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Amino acid: As used herein, the term "amino acid," in its broadest sense, refers to any compound and/or substance that can be incorporated into a polypeptide chain. In some embodiments, an amino acid has the general structure $H_2N$—$C(H)(R)$—COOH. In some embodiments, an amino acid is a naturally occurring amino acid. In some embodiments, an amino acid is a modified amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "modified amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or more post-translational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" refers to delivery of a composition to an organism, including but not limited to an animal or human. For delivery to a multi-tissue organism, delivery encompasses both local and systemic delivery. For example, delivery of a nucleic acid such as mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into a patient's circulation system (e.g., serum) and systematically distributed and taken up by other tissues (also referred to as "systemic distribution" or "systemic delivery").

Expression: As used herein, "expression" of a nucleic acid sequence refers to translation of an mRNA into a protein, such as an antigen (e.g., from an infectious agent or cancer cell), an enzyme, an antibody, an intrabody, an intracellularly acting protein, a cytosolic protein, a transmembrane protein, a membrane-bound protein, a secreted protein, a cell surface receptor or ligand, or a soluble receptor or ligand. Expression also can include the assembly of multiple proteins or polypeptides, e.g., into an intact protein, (e.g., an antibody) and/or post-translational modification of a protein or polypeptide into a functional biological molecule. In this application, the terms "expression" and "production," and grammatical equivalent, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" or "mRNA" refers to a polynucleotide that encodes at least one protein. As used herein, the term "protein" as being a product of mRNA expression is meant to encompass full length proteins, as well as functional fragments and variants thereof, polypeptides (e.g., an antibody light chain) and peptides (e.g., antigens) that are expressed from the mRNA. The term "mRNA" as used herein encompasses both mRNA having one more modified nucleotides, and mRNA having all unmodified nucleotides. mRNA may contain one or more coding and non-coding regions. mRNA can be purified from natural sources, produced using recombinant expression systems or plasmid-based expression systems or in vitro transcription (IVT) systems, and optionally purified and/or modified, or produced by chemical synthesis. In some embodiments, for example, for mRNA produced using recombinant or plasmid-based expression systems or produced by chemical synthesis, the mRNA coding region, the mRNA non-coding region, or both the mRNA coding and non-coding regions, can include a unique nucleic acid sequence (having modified or unmodified nucleic acids), i.e., that is different from natural and/or known nucleic acid sequences for that mRNA. For example, in some embodiments, the mRNA coding region can include one or more codons that have a different triplet nucleic acid sequence than the triplet nucleic acid sequence of the corresponding codons in the corresponding natural or known mRNA (referred to herein as a "codon-optimized" sequence). An mRNA sequence is presented in the 5' to 3' direction unless otherwise indicated. In some embodiments, "mRNA" as used herein can encompass both unmodified RNA and modified mRNA (mmRNA). The modifications in mmRNA can comprise nucleoside analogs such as analogs having one or more chemically modified bases or sugars, backbone modifications, or other modifications described herein. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C5-propynyl-cytidine, C5-propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O-6-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses ribonucleic acids (RNA), including but not limited to any one or more of interference RNAs (RNAi), small interfering RNA (siRNA), short hairpin RNA (shRNA), antisense RNA (aRNA), messenger RNA (mRNA), modified messenger RNA (mmRNA), unmodified messenger RNA (umRNA), long non-coding RNA (lncRNA), micro-RNA (miRNA) multimeric coding nucleic acid (MCNA), polymeric coding nucleic acid (PCNA), guide RNA (gRNA) and CRISPR RNA (crRNA). In some embodiments, "nucleic acid" encompasses deoxyribonucleic acid (DNA), including but not limited to any one or more of single-stranded DNA (ssDNA), double-stranded DNA (dsDNA) and complementary DNA (cDNA). In some embodiments, "nucleic acid" encompasses both RNA and DNA. In embodiments, DNA may be in the form of antisense DNA, plasmid DNA, parts of a plasmid DNA, pre-condensed DNA, a product of a polymerase chain reaction (PCR), vectors (e.g., P1, PAC, BAC, YAC, artificial chromosomes), expression cassettes, chimeric sequences, chromosomal DNA, or derivatives of these groups. In embodiments, RNA may be in the form of messenger RNA (mRNA), ribosomal RNA (rRNA), signal recognition particle RNA (7 SL RNA or SRP RNA), transfer RNA (tRNA), transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P (RNase P), Y RNA, telomerase RNA component (TERC), spliced leader RNA (SL RNA), antisense RNA (aRNA or asRNA), cis-natural antisense transcript (cis-NAT), CRISPR RNA (crRNA), long noncoding RNA (lncRNA), micro-RNA (miRNA), piwi-interacting RNA (piRNA), small interfering RNA (siRNA), transacting siRNA (tasiRNA), repeat associated siRNA (rasiRNA), 73K RNA, retrotransposons, a viral genome, a viroid, satellite RNA, or derivatives of these groups. In some embodiments, a nucleic acid is a mRNA encoding a protein such as an enzyme.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quaternized alkylated amino salt.

Systemic distribution or delivery: As used herein, the terms "systemic distribution," "systemic delivery," or grammatical equivalent, refer to a delivery or distribution mechanism or approach that affect disparate compartments or tissues of the entire body or of an entire organism. Typically, systemic distribution or delivery is accomplished via a body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one-unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the aliphatic is unsubstituted. In embodiments, the aliphatic does not include any heteroatoms.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, isohexyl, etc. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the alkyl is unsubstituted. In embodiments, the alkyl is substituted (e.g., with 1, 2, 3, 4, 5, or 6 substituent groups as described herein).

Alkylene: The term "alkylene," as used herein, represents a saturated divalent straight or branched chain hydrocarbon group, e.g., a "$C_1$-$C_{10}$ alkylene" group having 1-10 carbons. Alkylene groups are exemplified by methylene, ethylene, isopropylene and the like. An alkylene may be unsubstituted or substituted with substituent groups as described herein. In embodiments, an alkylene group is unsubstituted Alkaryl: The term "alkaryl," as used herein, represents a $C_1$-$C_6$ alkyl group having a $C_6$-$C_{10}$ aryl or a 5- to 10-membered heteroaryl located at any position of the carbon chain. In embodiments, an alkaryl group comprises a $C_6$-$C_{10}$ aryl. In embodiments, an alkaryl group comprises a 5- to 10-membered heteroaryl. The $C_1$-$C_6$ alkyl group may be linear or branched. An alkaryl group may be unsubstituted or substituted with, for example, 1, 2, 3, 4, or 5 substituents on the alkyl group and/or on the aryl or heteroaryl moiety. Exemplary alkaryl groups include benzyl, phenethyl, and —$CH_2C_6H_4{}^tBu$.

Alkenyl: As used herein, "alkenyl" means any linear or branched hydrocarbon chains having one or more unsaturated carbon-carbon double bonds that may occur in any stable point along the chain, e.g., "$C_2$-$C_{20}$ alkenyl" refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In embodiments, the alkenyl comprises 1, 2, or 3 carbon-carbon double bond. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the alkenyl is unsubstituted. In embodiments, the alkenyl is substituted (e.g., with 1, 2, 3, 4, 5, or 6 substituent groups as described herein).

Alkynyl: As used herein, "alkynyl" means any hydrocarbon chain of either linear or branched configuration, having one or more carbon-carbon triple bonds occurring in any stable point along the chain, e.g., "$C_2$-$C_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In embodiments, an alkynyl comprises a carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —CO$_2$R', —CN, —OH, —OR', —NH$_2$, —NHR', —N(R')$_2$, —SR' or —SO$_2$R', wherein each instance of R' independently is C$_1$-C$_3$ alkyl. In embodiments, the alkynyl is unsubstituted. In embodiments, the alkynyl is substituted (e.g., with 1, 2, 3, 4, 5, or 6 substituent groups as described herein).

Cycloalkyl: As used herein, the term "cycloalkyl" means a non-aromatic, saturated, cyclic group, e.g. "C$_3$-C$_{10}$ cycloalkyl." In embodiments, a heterocyclyl is monocyclic. In embodiments, a heterocyclyl is polycyclic (e.g., bicyclic or tricyclic). In polycyclic cycloalkyl groups, individual rings can be fused, bridged, or spirocyclic. Examples of a cycloalkyl group include cyclopropyl, cyclobutyl, cyclopentyl, cyclohexyl, norbornanyl, bicyclo[3.2.1]octanyl, octahydro-pentalenyl, and spiro[4.5]decanyl, and the like. The term "cycloalkyl" may be used interchangeably with the term "carbocycle." A cycloalkyl group may be unsubstituted or substituted with one or more substituent groups as described herein. For example, a cycloalkyl group may be substituted with one or more (e.g., 1, 2, 3, 4, 5, or 6 independently selected substituents) of halogen, —CO$_2$R', —CN, —OH, —OR', —NH$_2$, —NHR', —N(R')$_2$, —SR' or —SO$_2$R', wherein each instance of R' independently is C$_1$-C$_3$ alkyl. In embodiments, the cycloalkyl is unsubstituted. In embodiments, the cycloalkyl is substituted (e.g., with 1, 2, 3, 4, 5, or 6 substituent groups as described herein).

Halogen: As used herein, the term "halogen" means fluorine, chlorine, bromine, or iodine.

Heterocyclyl: As used herein, the term "heterocyclyl" means a non-aromatic, cyclic structure having at least one of any type of heteroatom as ring atoms, having any degree of unsaturation, and excludes aromatic heterocyclic rings that are defined as "heteroaryl" herein. For example, a "3- to 10-membered heterocyclyl" refers to heterocyclics having 3-10 ring atoms that are carbon or heteroatoms as described herein. The one or more heteroatoms may be selected from nitrogen, sulfur, and oxygen. The term "heterocycle," "heterocyclyl," "heterocyclic," "heterocycloalkyl," and "heterocyclic ring" can be used interchangeably. A heterocyclyl group can be attached as a substituent via a carbon atom or a heteroatom (e.g. a nitrogen atom). In embodiments, a heterocyclyl is monocyclic. In embodiments, a heterocyclyl is polycyclic (e.g., bicyclic or tricyclic). Examples include 2-tetrahydrofuranyl, 3-tetrahydrofuranyl, dihydrofuranyl, tetrahydropyranyl, pyranyl, thiopyranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 1,3-oxazolidin-3-yl, isothiazolidinyl, 1,3-thiazolidin-3-yl, 1,2-pyrazolidin-2-yl, 1,3-pyrazolidin-1-yl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperizin-2-onyl, piperizin-3-onyl, 2-pyrrolinyl, 3-pyrrolinyl, imidazolidinyl, 2-imidazolidinyl, 1,4-dioxanyl, and 4-thiazolidinyl, and the like. A heterocyclyl group may be unsubstituted or substituted with one or more substituent groups as described herein. For example, a heterocyclyl group may be substituted with one or more (e.g., 1, 2, 3, 4, 5, or 6 independently selected substituents) of halogen, —CO$_2$R', —CN, —OH, —OR', —NH$_2$, —NHR', —N(R')$_2$, —SR' or —SO$_2$R', wherein each instance of R' independently is C$_1$-C$_3$ alkyl. In embodiments, the heterocyclyl is unsubstituted. In embodiments, the heterocyclyl is substituted (e.g., with 1, 2, 3, 4, 5, or 6 substituent groups as described herein).

Heteroaryl: As used herein, the term "heteroaryl" means an aromatic moiety having at least one of any type of heteroatom as ring atoms. For example, a "5- to 14-membered heteroaryl" refers to heteroaryls having 5-14 ring atoms that are carbon or heteroatoms as described herein. The one or more heteroatoms may be selected from nitrogen, sulfur, and oxygen. A heteroaryl group can be attached as a substituent via a carbon atom or a heteroatom (e.g. a nitrogen atom). In embodiments, a heteroaryl is monocyclic. In embodiments, a heteroaryl is polycyclic (e.g., bicyclic or tricyclic). In embodiments, polycyclic heteroaryls comprise a cyclic group that is non-aromatic (e.g., a heteroaryl fused to a cycloalkyl or a heterocyclyl group as described herein). The term "heteroaryl" may be used interchangeably with the term "heteroaryl ring" or the term "heteroaromatic". Examples include 5-membered monocyclic rings such as pyrrolyl, imidazolyl, pyrazolyl, triazolyl, furyl, oxazolyl, isoxazolyl, oxadiazolyl, thiadiazolyl, thiazolyl, isothiazolyl, and the like; and 6-membered monocyclic rings such as pyridyl, pyrazinyl, pyrimidinyl, pyridazinyl, triazinyl and the like. For further examples, see e.g. Katritzky, Handbook of Heterocyclic Chemistry. Further specific examples of heteroaryl rings include 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl and carbazolyl. The term "heteroaryl" also refers to rings that are optionally substituted. A heteroaryl group may be optionally substituted with one or more functional groups discussed below. Still other examples include indolyl, azaindolyl, benzimidazolyl, indazolyl, imidazopyridinyl, imidazopyrimidinyl, pyrrolopyrimidinyl, pyrrolopyridinyl, pyrazolopyridinyl, pyrazolopyrimidinyl, quinolyl, isoquinolyl, benzoxazolyl, benzothiazolyl, benzothiophenyl, benzofuranyl, and isobenzofuranyl, and the like. A heteroaryl group may be unsubstituted or substituted with one or more substituent groups as described herein. For example, a heteroaryl group may be substituted with one or more (e.g., 1, 2, 3, 4, 5, or 6 independently selected substituents) of halogen, —CO$_2$R', —CN, —OH, —OR', —NH$_2$, —NHR', —N(R')$_2$, —SR' or —SO$_2$R', wherein each instance of R' independently is C$_1$-C$_3$ alkyl. In embodiments, the heteroaryl is unsubstituted. In embodiments, the heteroaryl is substituted (e.g., with 1, 2, 3, 4, 5, or 6 substituent groups as described herein).

Nitrogen-protecting groups (N-protecting groups): The use of protecting groups for nitrogen functional groups (e.g., amino groups) is well known in the art and include those described in detail in Protecting Groups in Organic Synthesis, T. W. Greene and P. G. M. Wuts, 3rd edition, John Wiley & Sons, 1999, and exemplary groups described in US2017/0246319, which are both incorporated herein by reference. These groups are useful in modulating the reactivity of the original functional group. In certain embodiments, the substituent present on a nitrogen atom is a nitrogen protecting group (also referred to as an amino protecting group). Nitrogen protecting groups include, but are not limited to, —OR", —N(R")$_2$, —C(=O)R", —C(=O)N(R")$_2$, —CO$_2$R", —SO$_2$R", —C(=NR")R", —C(=NR")OR", —C(αNR")N(R")$_2$, —SO$_2$N(R")$_2$, —SO$_2$R", —SO$_2$OR", —SOR", —C(=S)N(R")$_2$, —C(=O)SR", —C(=S)SR", wherein each R" is independently hydrogen, alkaryl, $C_1$-$C_{10}$ alkyl, $C_2$-$C_{10}$ alkenyl, $C_2$-$C_{10}$ alkynyl, $C_3$-$C_{10}$ cycloalkyl, 3- to 14-membered heterocyclyl, $C_6$-$C_{14}$ aryl, or 5- to 14-membered heteroaryl as defined herein. In embodiments, each R" is independently alkaryl, $C_1$-$C_{10}$ alkyl, $C_2$-$C_{10}$ alkenyl, $C_2$-$C_{10}$ alkynyl, $C_3$-$C_{10}$ cycloalkyl, 3- to 14-membered heterocyclyl, $C_6$-$C_{14}$ aryl, or 5- to 14-membered heteroaryl.

In embodiments, N-protecting groups include: acyl protecting groups (e.g., acetyl and benzoyl); alkaryl protecting groups (e.g., benzyl; p-methoxybenzyl; or 3,4-dimethoxybenzyl); aryl protecting groups (e.g., p-methoxyphenyl); carbamate protecting groups (e.g., tert-butyloxycarbonyl (BOC); carbobenzyloxy (Cbz); p-methoxybenzyl carbonyl; 9-fluorenylmethyloxycarbonyl (FMOC); or 2,2,2-trichlorethoxy carbonyl (TROC)); and sulfonyl protecting groups (e.g., p-toluenesulfonyl (Ts) or p-nitrobenzenesulfonyl (Ns)).

For example, acyl protecting groups (e.g., —C(=O)R") include, but are not limited to, formyl, acetyl, chloroacetyl, trichloroacetyl, trifluoroacetyl, phenylacetyl, 3-phenylpropanoyl, acetopyridine, benzoyl, p-phenylbenzoyl, p-nitrobenzoyl, o-nitrobenzoyl, acetoacetyl, (N'-dithiobenzyloxyacylamino) acetyl, 3-(p-hydroxyphenyl)propanoyl, 3-(o-nitrophenyl)propanoyl, 2-methyl-2-(o-nitrophenoxy)propanoyl, 2-methyl-2-(o-phenylazophenoxy)propanoyl, 4-chlorobutanoyl, 3-methyl-3-nitrobutanoyl, o-nitrocinnamoyl, N-acetylmethionine derivative, and o-(benzoyloxymethyl)benzoyl. In embodiments, an acyl protecting group is acetyl or benzoyl.

Carbamate protecting groups (e.g., —C(=O)OR") include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate. In embodiments, a carbamate protecting group is t-butyl carbamate (BOC); benzyl carbamate (Cbz); p-methoxybenzyl carbamate (Moz); 9-fluorenylmethyl carbamate (Fmoc); or 2,2,2-trichloroethyl carbamate (Troc).

Sulfonyl protecting groups (e.g., —S(=O)$_2$R") include, but are not limited to, p-toluenesulfonyl (Ts), benzenesulfonyl, 2,3,6,-trimethyl-4-methoxybenzenesulfonyl (Mtr), 2,4,6-trimethoxybenzenesulfonyl (Mtb), 2,6-dimethyl-4-methoxybenzenesulfonyl (Pme), 2,3,5,6-tetramethyl-4-methoxybenzenesulfonyl (Mte), 4-methoxybenzenesulfonyl (Mbs), 2,4,6-trimethylbenzenesulfonyl (Mts), 2,6-dimethoxy-4-methylbenzenesulfonyl (iMds), 2,2,5,7,8-pentamethylchroman-6-sulfonyl (Pmc), methanesulfonyl (Ms), f3-trimethylsilylethanesulfonyl (SES), 9-anthracenesulfonyl, 4-(4',8'-dimethoxynaphthylmethyl)benzenesulfonyl (DNMBS), benzylsulfonyl, trifluoromethylsulfonyl (Tf), and phenacylsulfonyl. In embodiments, a sulfonyl protecting group is p-toluenesulfonyl (Ts) or p-nitrobenzenesulfonyl (Ns).

Oxygen-protecting groups (O-protecting groups): The use of protecting groups for oxygen functional groups (e.g., hydroxy groups or carboxy acid groups) is well known in the art and include those described in detail in Protecting Groups in Organic Synthesis, T. W. Greene and P. G. M. Wuts, 3rd edition, John Wiley & Sons, 1999, and exemplary groups described in US2017/0246319, which are both incorporated herein by reference. These groups are useful in modulating the reactivity of the original functional group. Oxygen protecting groups include, but are not limited to, —R", —N(R")$_2$, —C(=O)SR", —C(=O)R", —CO$_2$R", —C(=O)N(R")$_2$, —C(=NR")R", —C(=NR")OR", —C(=NR")N(R")$_2$, —S(=O)R", —SO$_2$R", Si(R")$_3$, —P(R")$_2$, —P(R")$_3$, —P(=O)$_2$R", —P(=O)(R")$_2$, —P(=O)(OR")$_2$, —P(=O)$_2$N(R")$_2$, and —P(=O)(NR")$_2$, wherein each R" is independently hydrogen, alkaryl, $C_1$-$C_{10}$ alkyl, $C_2$-$C_{10}$ alkenyl, $C_2$-$C_{10}$ alkynyl, $C_3$-$C_{10}$ cycloalkyl, 3- to 14-membered heterocyclyl, $C_6$-$C_{14}$ aryl, or 5- to 14-membered heteroaryl as defined herein. In embodiments, each R" is independently alkaryl, $C_1$-$C_{10}$ alkyl, $C_2$-$C_{10}$ alkenyl, $C_2$-$C_{10}$ alkynyl, $C_3$-$C_{10}$ cycloalkyl, 3- to 14-membered heterocyclyl, $C_6$-$C_{14}$ aryl, or 5- to 14-membered heteroaryl.

Exemplary O-protecting groups include: acyl protecting groups (e.g., acetyl, benzoyl, or pivaloyl); alkaryl protecting groups (e.g., benzyl or p-methoxybenzyl (PMB)); alkoxyalkyl protecting groups (e.g., methoxymethyl (MOM) or O-methoxyethoxymethyl (MEM)); alkyl protecting groups (e.g., methyl, ethyl, or tert-butyl); heterocyclic protecting groups (e.g., tetrahydropyran (THP) ether or tetrahydrofuran (THF) ether); silyl protecting groups (e.g., trimethylsilyl (TMS); tert-butyldimethylsilyl (TBDMS); or triisopropylsilyl (TIPS)); thioalkoxyalkyl ether protecting groups (e.g., methylthiomethyl ether); and trityl protecting groups (e.g., —C(Ph)$_3$ (trityl); methoxytrityl (MMT) or dimethoxytrityl (DMT)). In embodiments, a hydroxyl protecting group is an acyl group, an alkaryl group, an alkoxyalkyl group, a heterocyclic group, a silyl group, or a trityl group. In embodiments, a carboxy acid protecting group is an alkyl group, an alkaryl group, or a silyl group. In embodiments, acyl protecting groups protecting groups include those described herein for N-protecting groups.

For example, oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl) methyl, 3-(imidazol-1-yl)bis(4',4"-dimethoxyphenyl) methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Polymers

Provided herein are cationic polymers, including compositions thereof, and methods for the preparation and use of these polymers. The polymers described herein can have various beneficial features and properties as described herein.

In one aspect, the invention features a polymer that comprises monomers having the following structure:

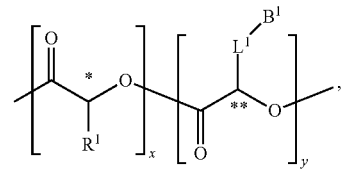

wherein
$R^1$ is $C_6$-$C_{20}$ alkyl, $C_6$-$C_{20}$ alkenyl, or $C_6$-$C_{20}$ alkynyl;
$L^1$ is $C_2$-$C_{20}$ alkylene;
$B^1$ is $NR^2R^3$ or a 5- to 10-membered heteroaryl group;
$R^2$ is hydrogen or $C_1$-$C_{20}$ alkyl;
$R^3$ is hydrogen, $C_1$-$C_{20}$ alkyl, or an N-protecting group;
or $R^2$ and $R^3$, together with the nitrogen to which they are attached, combine to form a 5- to 10-membered heterocyclic group;
x is an integer of 5 to 500; and
y is an integer of 5 to 500.

In embodiments, each of x and y is independently an integer of 5 to 100, 5 to 200, 5 to 300, or 5 to 400. In embodiments, each of x and y is independently an integer of 5 to 250, 5 to 200, 5 to 150, 5 to 100, 5 to 50, 10 to 200, 10 to 150, 10 to 100, 10 to 50, 20 to 250, 20 to 200, 20 to 150, 20 to 100, or 20 to 50. In embodiments, each of x and y is independently an integer of 25 to 500, 25 to 400, 25 to 300, 25 to 200, 25 to 100, 50 to 500, 50 to 400, 50 to 300, 50 to 200, or 50 to 100.

In embodiments, x=y.

In embodiments, the polymer comprises the repeating unit

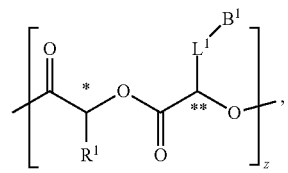

where z is an integer of 5 to 500.

In embodiments, z is an integer of 5 to 100, 5 to 200, 5 to 300, or 5 to 400. In embodiments, z is an integer of 5 to 250, 5 to 200, 5 to 150, 5 to 100, 5 to 50, 10 to 200, 10 to 150, 10 to 100, 10 to 50, 20 to 250, 20 to 200, 20 to 150, 20 to 100, or 20 to 50. In embodiments, z is an integer of 25 to 500, 25 to 400, 25 to 300, 25 to 200, 25 to 100, 50 to 500, 50 to 400, 50 to 300, 50 to 200, or 50 to 100.

In embodiments, a polymer described herein comprises an end group $R^4$ that is attached to a —O— moiety, and an end group —$OR^5$ that is attached to a carbonyl moiety, wherein $R^4$ and $R^5$ are each independently hydrogen, $C_1$-$C_{12}$ alkyl, or $C_7$-$C_{12}$ alkaryl. In embodiments, a polymer described herein comprises an end group $R^4$ that is attached to a —O— moiety, and an end group —$OR^5$ that is attached to a carbonyl moiety, wherein $R^4$ is hydrogen, and $R^5$ is —$CH_2C_6H_4{}^tBu$.

In embodiments, the polymer has the following structure

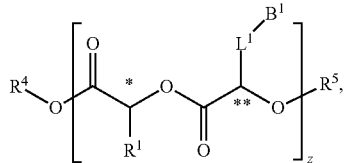

where $R^4$ and $R^5$ are each independently hydrogen, $C_1$-$C_{12}$ alkyl, or $C_7$-$C_{12}$ alkaryl.

In embodiments, $R^4$ is hydrogen.

In embodiments, $R^5$ is hydrogen, —$CH_2C_6H_5$, or —$CH_2C_6{}^tBu$.

In embodiments, $R^1$ is unsubstituted $C_6$-$C_{14}$ alkyl or unsubstituted $C_6$-$C_{10}$ alkyl.

In embodiments, $B^1$ is a heteroaryl group. In embodiments, $B^1$ is pyrrolyl, imidazolyl, pyrazolyl, oxazolyl, isoxazolyl, thiazolyl, isothiazolyl, pyridinyl, pyrazinyl, pyrimidinyl, or pyridazinyl. In embodiments, $B^1$ is imidazolyl.

In embodiments, $B^1$ is $NR^2R^3$. In embodiments, $R^2$ and $R^3$, together with the nitrogen to which they are attached, combine to form a 5- to 10-membered heterocyclic group. In embodiments, $R^2$ is independently hydrogen or $C_1$-$C_{20}$ alkyl; and $R^3$ is independently hydrogen, $C_1$-$C_{20}$ alkyl, or an N-protecting group. In embodiments, $R^2$ is hydrogen. In embodiments, $R^3$ is unsubstituted $C_1$-$C_6$ alkyl. In embodiments, $R^3$ is —$C(O)O(CH_3)_3$.

In embodiments, L is independently unsubstituted $C_2$-$C_{10}$ alkylene. In embodiments, $L^1$ is —$CH_2CH_2$—.

In embodiments, the carbon marked by the single asterisk * has the R stereoconfiguration.

In embodiments, the carbon marked by the single asterisk * has the S stereoconfiguration.

In embodiments, the carbon marked by the double asterisk ** has the S stereoconfiguration.

In embodiments, the carbon marked by the double asterisk ** has the R stereoconfiguration.

In embodiments, the carbon marked by the single asterisk * has the R stereoconfiguration, and the carbon marked by the double asterisk ** has the S stereoconfiguration. In embodiments, the carbon marked by the single asterisk * has the S stereoconfiguration, and the carbon marked by the double asterisk ** has the S stereoconfiguration.

In embodiments, the polymer comprises the following monomers,

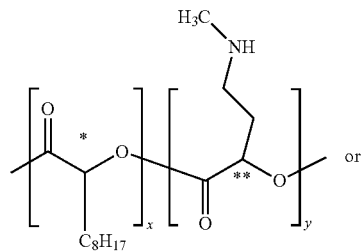

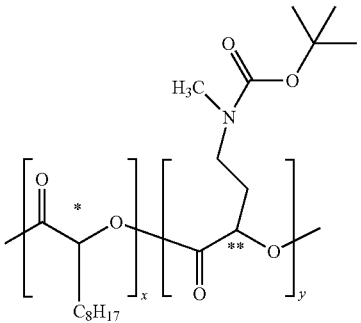

In embodiments, the polymer comprises the following monomers,

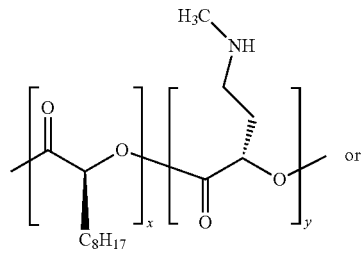

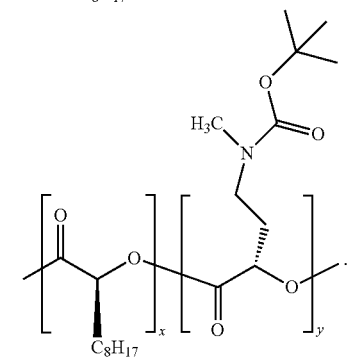

In embodiments, the polymer comprises the following monomers,

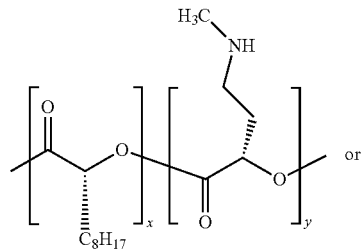

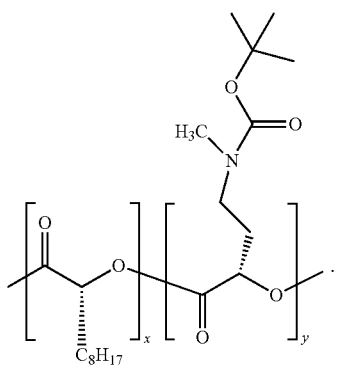

In embodiments, the polymer comprises a repeating unit that is:

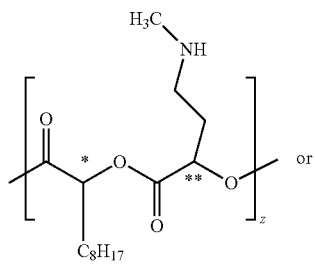

In embodiments, the polymer comprises a repeating unit that is:

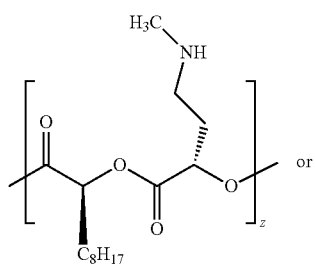

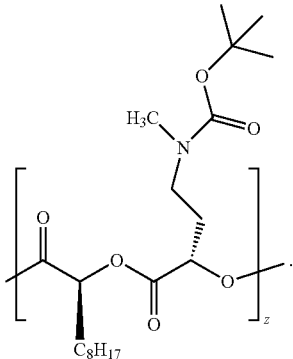

In embodiments, the polymer comprises a repeating unit that is:

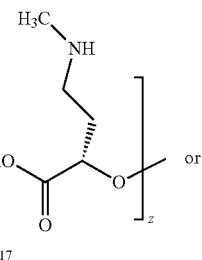

In embodiments, the polymer has a $M^W$ of about 1,000 Da to about 40,000 Da. In embodiments, the polymer has a $M_W$ of about 1,000 Da to about 20,000 Da, about 1,000 Da to about 30,000 Da, or about 1,000 Da to about 10,000 Da. In embodiments, the polymer has a $M_W$ of about 5,000 Da to about 10,000 Da, about 5,000 Da to about 15,000 Da, about 5,000 Da to about 20,000 Da, or about 5,000 Da to about 25,000 Da.

In embodiments, the polymer has a net neutral charge.

In embodiments, the polymer has a net cationic charge. In embodiments, the polymer comprises trifluoroacetate counterions.

In another aspect, the invention features a method of synthesizing polymers described herein, where the method comprises the following ring-opening polymerization (ROP),

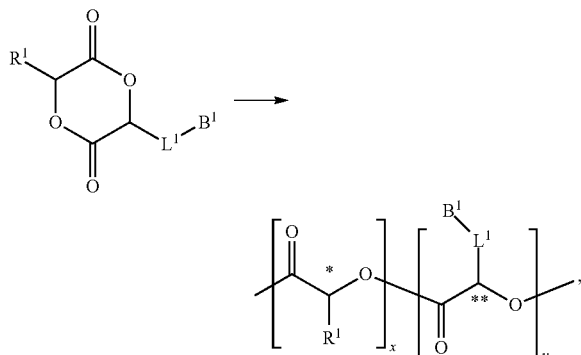

where $R^1$, $L^1$, $B^1$, x, and y are as defined in any embodiment described herein.

In embodiments, the ring opening polymerization is mediated by a Zn(II) compound.

In another aspect, the invention features a polymer comprising a repeating unit having the following structure,

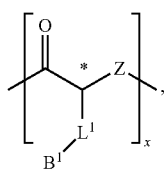

where
$L^1$ is $C_2$-$C_{20}$ alkylene;
Z is O or $NR^4$;
$B^1$ is $NR^2R^3$ or a 5- to 10-membered heteroaryl group;
each of $R^2$ and $R^3$ is independently hydrogen or $C_1$-$C_{20}$ alkyl; or $R^2$ and $R^3$, together with the nitrogen to which they are attached, combine to form a 5- to 10-membered heterocyclic group;
$R^4$ is hydrogen or $C_1$-$C_{20}$ alkyl; and
x is an integer of 5 to 1000.

In embodiments, x is an integer of 5 to 100, 5 to 200, 5 to 300, 5 to 400, 5 to 500, 5 to 600, 5 to 700, 5 to 800, or 5 to 900. In embodiments, x is an integer of 5 to 450, 5 to 400, 5 to 350, 5 to 300, 5 to 250, 5 to 200, 5 to 150, 5 to 100, 5 to 50, 10 to 200, 10 to 150, 10 to 100, 10 to 50, 20 to 250, 20 to 200, 20 to 150, 20 to 100, or 20 to 50. In embodiments, x is an integer of 25 to 500, 25 to 400, 25 to 300, 25 to 200, 25 to 100, 50 to 500, 50 to 400, 50 to 300, 50 to 200, or 50 to 100.

In embodiments, the repeating unit has the following structure:

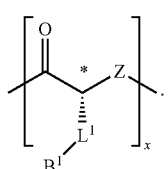

In embodiments, the repeating unit has the following structure:

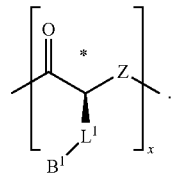

In another aspect, the invention features a polymer comprising two different monomers having the following structure,

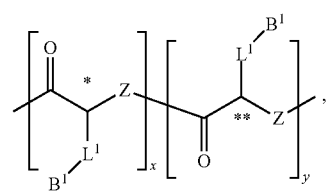

wherein,
$L^1$ is independently $C_2$-$C_{20}$ alkylene;
Z is O or $NR^4$;
$B^1$ is $NR^2R^3$ or a 5- to 10-membered heteroaryl group;
each of $R^2$ and $R^3$ is independently hydrogen or $C_1$-$C_{20}$ alkyl; or $R^2$ and $R^3$, together with the nitrogen to which they are attached, combine to form a 5- to 10-membered heterocyclic group;
$R^4$ is hydrogen or $C_1$-$C_{20}$ alkyl;
x is an integer of 5 to 500;
y is an integer of 5 to 500; and
wherein the two monomers differ in the identity of -$L^1B^1$ or Z, or in the stereochemistry of the carbon marked by the single asterisk and the carbon marked by the double asterisk.

In embodiments, each of x and y is independently an integer of 5 to 100, 5 to 200, 5 to 300, or 5 to 400. In embodiments, each of x and y is independently an integer of 5 to 250, 5 to 200, 5 to 150, 5 to 100, 5 to 50, 10 to 200, 10 to 150, 10 to 100, 10 to 50, 20 to 250, 20 to 200, 20 to 150, 20 to 100, or 20 to 50. In embodiments, each of x and y is independently an integer of 25 to 500, 25 to 400, 25 to 300, 25 to 200, 25 to 100, 50 to 500, 50 to 400, 50 to 300, 50 to 200, or 50 to 100.

In embodiments, x=y.

In embodiments, the two different monomers have the following structure:

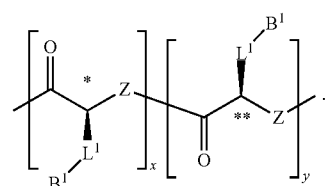

In embodiments, the two different monomers have the following structure:

In embodiments, the two different monomers have the following structure:

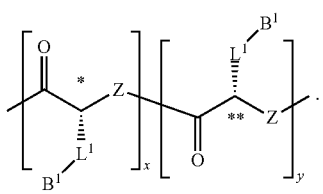

In embodiments, the two different monomers have the following structure:

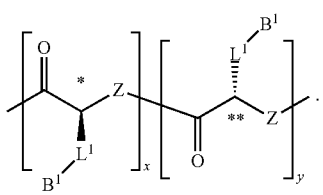

In embodiments, the two different monomers have the following structure:

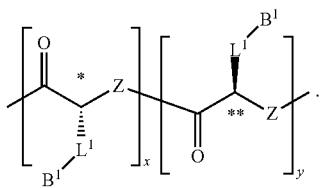

In embodiments, the polymer comprises a repeating unit having the following structure:

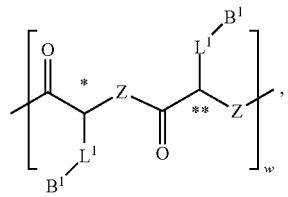

where w is an integer of 5 to 500.

In embodiments, the polymer comprises a repeating unit having the following structure:

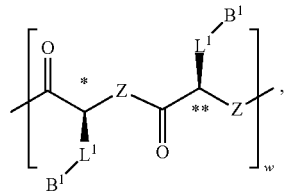

In embodiments, the polymer comprises a repeating unit having the following structure:

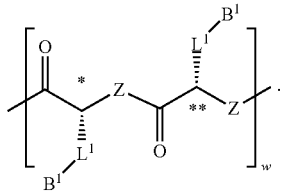

In embodiments, the polymer comprises a repeating unit having the following structure:

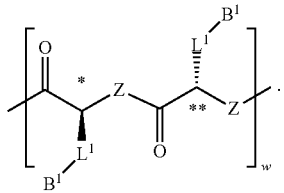

In embodiments, the polymer comprises a repeating unit having the following structure:

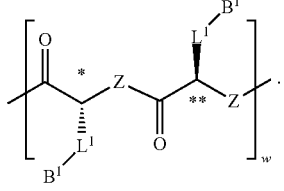

In embodiments, w is an integer of 5 to 100, 5 to 200, 5 to 300, or 5 to 400. In embodiments, w is an integer of 5 to 250, 5 to 200, 5 to 150, 5 to 100, 5 to 50, 10 to 200, 10 to 150, 10 to 100, 10 to 50, 20 to 250, 20 to 200, 20 to 150, 20 to 100, or 20 to 50. In embodiments, w is an integer of 25 to 500, 25 to 400, 25 to 300, 25 to 200, 25 to 100, 50 to 500, 50 to 400, 50 to 300, 50 to 200, or 50 to 100.

In embodiments, a polymer described herein comprises an end group $R^4$ that is attached to a —O— moiety, and an end group —$OR^5$ that is attached to a carbonyl moiety, wherein $R^4$ and $R^5$ are each independently hydrogen, $C_1$-$C_{12}$ alkyl, or $C_7$-$C_{12}$ alkaryl. In embodiments, a polymer described herein comprises an end group $R^4$ that is attached to a —O— moiety, and an end group —$OR^5$ that is attached to a carbonyl moiety, wherein $R^4$ is hydrogen, and $R^5$ is —$CH_2C_6H_4{}^tBu$.

In embodiments, each Z is O.

In embodiments, each Z is NH.

In embodiments, $L^1$ is substituted linear or branched $C_2$-$C_{10}$ alkylene.

In embodiments, $L^1$ is —$(CH_2)_4$—, —$(CH_2)_3CH(CH_3)$—, or —$(CH_3)CH(CH_2)_3$—.

In embodiments, $B^1$ is $NR^2R^3$.

In embodiments, each $R^2$ and $R^3$ is the same.

In embodiments, $R^2$ and $R^3$ are each substituted linear $C_{10}$-$C_{20}$ alkyl. In embodiments, each $R^2$ and $R^3$ is —$CH_2CH(OH)C_{10}H_{21}$.

In embodiments, the polymer comprises a repeating unit that is:

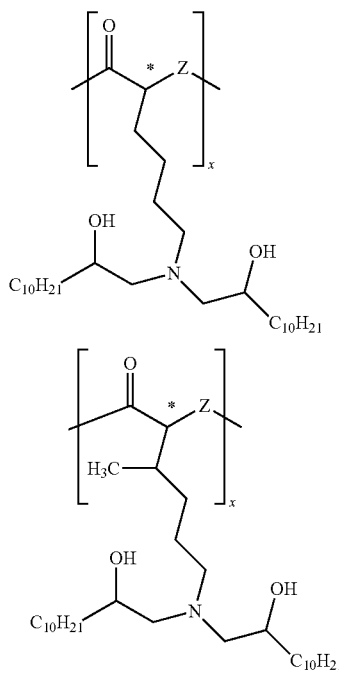

In embodiments, Z is O or NH. In embodiments, Z is O. In embodiments, Z is NH.

In embodiments, the polymer comprises a repeating unit that is:

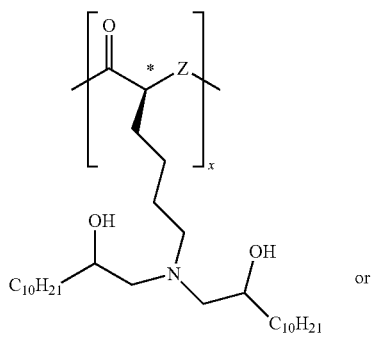

or

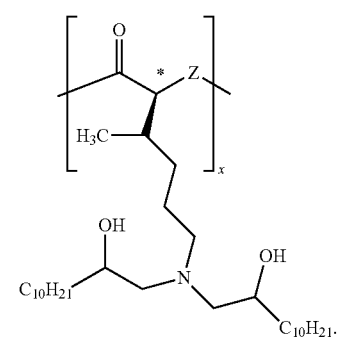

In embodiments, Z is O or NH. In embodiments, Z is O. In embodiments, Z is NH.

In embodiments, the polymer comprises a repeating unit that is:

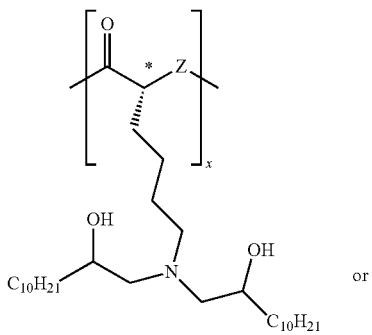

or

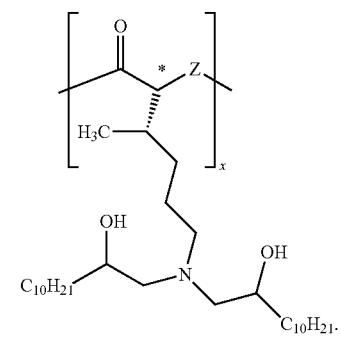

In embodiments, Z is O or NH. In embodiments, Z is O. In embodiments, Z is NH.

In embodiments, the polymer comprises a repeating unit that is:

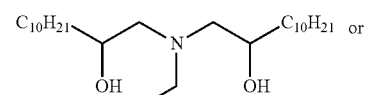

or

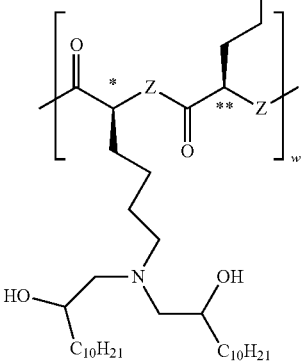

-continued
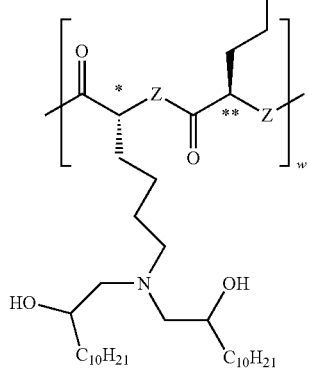
In embodiments, Z is O or NH. In embodiments, Z is O. In embodiments, Z is NH.
In embodiments, the polymer comprises a repeating unit that is:
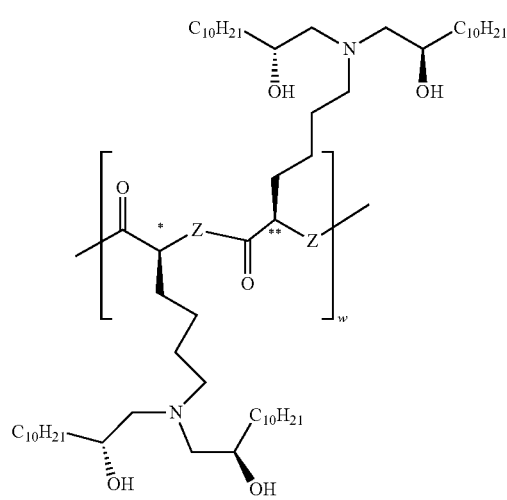
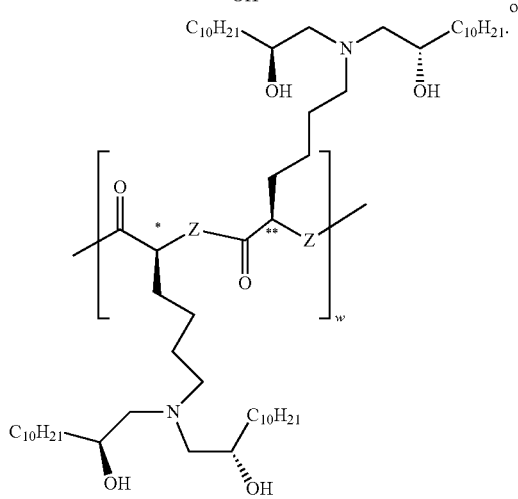
or
In embodiments, Z is O or NH. In embodiments, Z is O. In embodiments, Z is NH.
In embodiments, the polymer comprises a repeating unit that is:
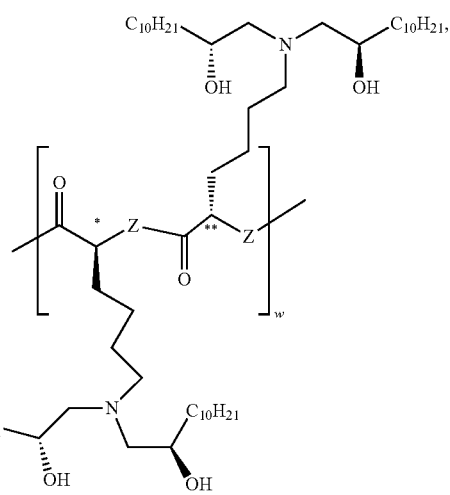
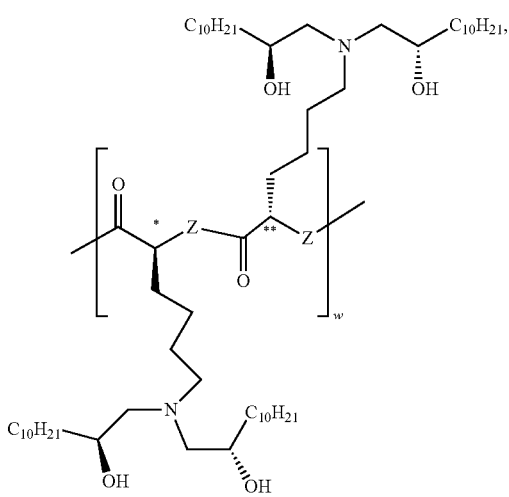
or
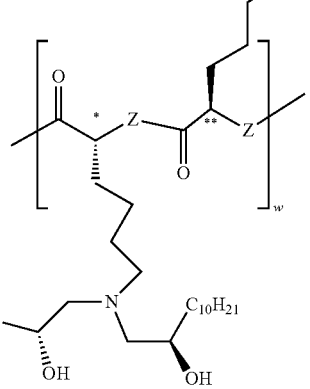

-continued

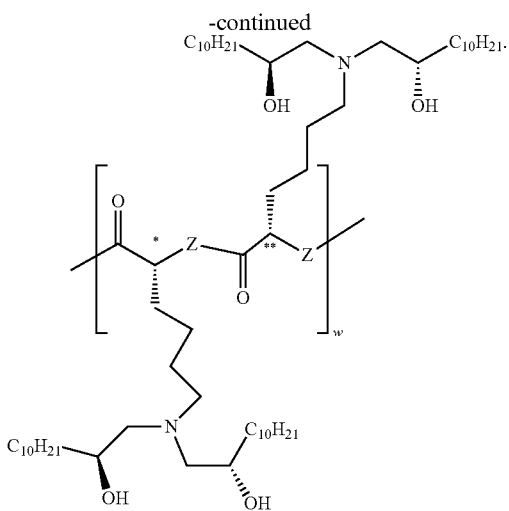

In embodiments, Z is O or NH. In embodiments, Z is O. In embodiments, Z is NH.

In another aspect, the invention features a compound having the following structure,

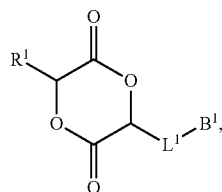

or a salt thereof, wherein
$R^1$ is $C_6$-$C_{20}$ alkyl, $C_6$-$C_{20}$ alkenyl, or $C_6$-$C_{20}$ alkynyl;
$L^1$ is $C_2$-$C_{20}$ alkylene;
$B^1$ is $NR^2R^3$ or a 5- to 10-membered heteroaryl group;
$R^2$ is hydrogen or $C_1$-$C_{20}$ alkyl;
$R^3$ is hydrogen, $C_1$-$C_{20}$ alkyl, or an N-protecting group; or
$R^2$ and $R^3$, together with the nitrogen to which they are attached, combine to form a 5- to 10-membered heterocyclic group.

In embodiments, the compound has a structure that is:

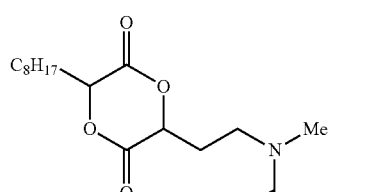

(1)

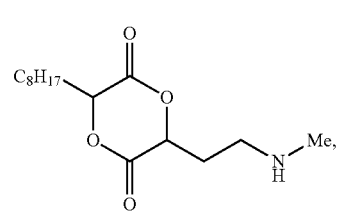

(2)

or a salt thereof.

In another aspect, the invention features a pharmaceutical composition comprising one or more polymers described herein and one or more polynucleotides, such as an mRNA. In embodiments, the pharmaceutical composition comprises a nanoparticle. In embodiments, the nanoparticle can be a lipid nanoparticle comprising one or more cationic lipids, one or more non-cationic lipids and one or more PEG-modified lipids. In embodiments, the lipid nanoparticle can encapsulate one or more polynucleotides, such as mRNA. In embodiments, the pharmaceutical composition comprises a nanoparticle that comprises one or more of the compounds described herein as well as one or more non-cationic lipids and one or more PEG-modified lipids, wherein the nanoparticle encapsulates one or more polynucleotides, such as mRNA. In embodiments, the pharmaceutical composition comprises one or more of the compounds described herein separate from a lipid nanoparticle that comprises one or more polynucleotides, such as mRNA.

In another aspect, the invention features a pharmaceutical composition comprising one or more of the polymers described herein; and one or more polynucleotides, such as mRNA. In embodiments, the pharmaceutical composition is a nanoparticle comprising one or more of the polymers described herein and encapsulating one or polynucleotides, such as mRNA.

In embodiments of the pharmaceutical compositions described herein, the one or more polynucleotides comprise mRNA. In embodiments, the RNA is selected from the group consisting of mRNA, siRNA, snoRNA, microRNA, gRNA, crRNA and combinations thereof. In embodiments, the mRNA encodes a protein, such as an antigen (e.g., from an infectious agent or cancer cell), an enzyme, an antibody, an intrabody, an intracellularly acting protein, a cytosolic protein, a transmembrane protein, a membrane-bound protein, a secreted protein, a cell surface receptor or ligand, or a soluble receptor or ligand.

In embodiments, the amount of a polymer in a composition is described as a molar ratio.

For example, the amount of polymer in a composition can be described as a percentage ("mol %") of the combined molar amounts of total lipids and polymer excipients of a composition (e.g., the combined molar amounts of all lipids and polymer excipients present in a lipid nanoparticle). In embodiments of pharmaceutical compositions described herein, the polymer is present in an amount that is about 0.5 mol % to about 20 mol % of the combined molar amounts of all lipids and polymer excipients present in a composition such as a lipid nanoparticle. In embodiments, the polymer is present in an amount that is about 0.5 mol % to about 5 mol %, about 1 mol % to about 10 mol %, about 5 mol % to about 20 mol %, or about 10 mol % to about 20 mol % of the combined molar amounts of all lipids and polymer excipients present in a composition such as a lipid nanoparticle.

In embodiments, the amount of a polymer in a composition is described as weight percentage ratio.

For example, the amount of polymer in a composition can be described as a percentage ("% (w/w)") of the combined dry weight of all lipids and polymer excipients of a composition (e.g., the combined dry weight of all lipids and polymer excipients present in a lipid nanoparticle). In embodiments of the pharmaceutical compositions described herein, the polymer is present in an amount that is about 0.5% (w/w) to about 20% (w/w) of the combined dry weight of all lipids and polymer excipients present in a composition such as a lipid nanoparticle.

In embodiments, the polymer is present in an amount that is about 5% (w/w) to about 10% (w/w) or about 10% (w/w)

to about 15% (w/w) of the combined dry weight of all lipids and polymer excipients present in a composition such as a lipid nanoparticle. In embodiments, the amount of polymer in a composition can be described as a percentage ("% (w/w)") of the combined dry weight of total polymer excipients in a composition (e.g., the combined dry weight of total polymer excipients in a lipid nanoparticle). In embodiments of the pharmaceutical compositions described herein, the polymer is present in an amount that is about 0.5% (w/w) to about 100% (w/w) of the combined dry weight of total polymer excipients in a composition such as a lipid nanoparticle. In embodiments, the polymer is present in an amount that is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of the combined dry weight of total polymer excipients in a composition such as a lipid nanoparticle.

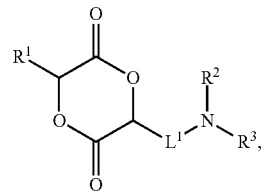

(Formula A)

or a salt thereof.

In embodiments, $R^1$, $L^1$, $R^2$, and $R^3$ are as described for any embodiment herein.

In embodiments, $R^1$ is independently $C_6$-$C_{20}$ alkyl, $C_6$-$C_{20}$ alkenyl, or $C_6$-$C_{20}$ alkynyl; $L^1$ is independently $C_2$-$C_{10}$ alkylene; $R^2$ is independently hydrogen or $C_1$-$C_6$ alkyl; and $R^3$ is independently hydrogen, $C_1$-$C_6$ alkyl, or an N-protecting group.

In embodiments, Compound A can be prepared according to Scheme 1.

Scheme 1

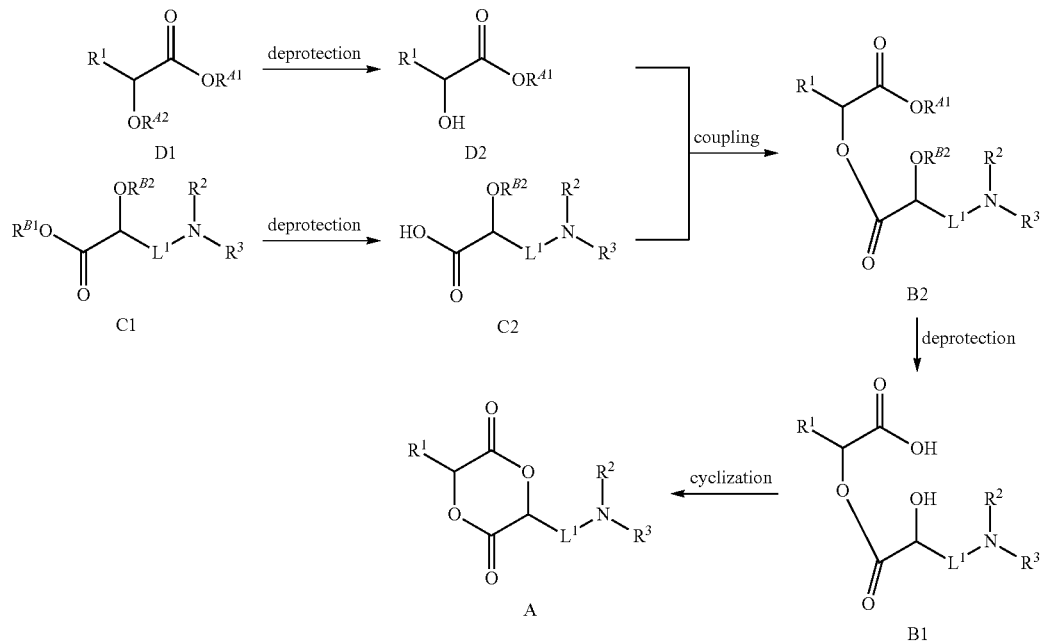

In embodiments, a pharmaceutical composition is formulated as a dry powder pharmaceutical composition.

In another aspect, the invention features a method of treating a disease in a subject, comprising administering to the subject an effective amount of any of the pharmaceutical compositions described herein.

Synthesis of Polymers

Polymers described herein can be prepared according to different methods known in the art.

In embodiments, polymers described herein can be prepared by ring-opening polymerization (ROP) of cyclic intermediates (e.g., cyclic ester or cyclic amide compounds).

For example, polymers described herein can be prepared via ROP of cyclic ester intermediates such as Formula A.

Pharmaceutically acceptable salts of any of the compounds described in Scheme 1 (e.g., a salt of any one of formulas A, B1, B2, C1, C2, D1, and D2) are also encompassed by and can be used in this exemplary synthesis.

Each of $R^{A1}$, $R^{A2}$, $R^{B1}$, and $R^{B2}$ is independently hydrogen or an O-protecting group.

In embodiments, each of $R^{A1}$ and $R^{B1}$ is independently hydrogen or an O-protecting group that is an alkyl group, an alkaryl group, or a silyl group.

In embodiments, each of $R^{A2}$ and $R^{B2}$ is independently hydrogen or an O-protecting group that is an acyl group, an alkaryl group, an alkoxyalkyl group, a heterocyclic group, a silyl group, or a trityl group.

In embodiments, $R^{A1}$ is hydrogen or an alkyl group (e.g., methyl or ethyl).

In embodiments, $R^{A2}$ is hydrogen or an alkaryl group (e.g., benzyl).

In embodiments, $R^{B1}$ is hydrogen or an alkaryl group (e.g., benzyl).

In embodiments, $R^{B2}$ is hydrogen.

In embodiments, $R^1$, $L^1$, $R^2$, and $R^3$ are as described for any embodiment herein.

In embodiments, $R^1$ is independently $C_6$-$C_{20}$ alkyl, $C_6$-$C_{20}$ alkenyl, or $C_6$-$C_{20}$ alkynyl; $L^1$ is independently $C_2$-$C_{10}$ alkylene; $R^2$ is independently hydrogen or $C_1$-$C_6$ alkyl; and $R^3$ is independently hydrogen, $C_1$-$C_6$ alkyl, or an N-protecting group.

In embodiments, $R^3$ is an N-protecting group (e.g., a carbamate group such as tert-butyloxycarbonyl (BOC); carbobenzyloxy (Cbz); p-methoxybenzyl carbonyl; or 9-fluorenylmethyloxy carbonyl (FMOC).

Scheme 2 shows a representative ROP reaction for preparation of polymers described herein.

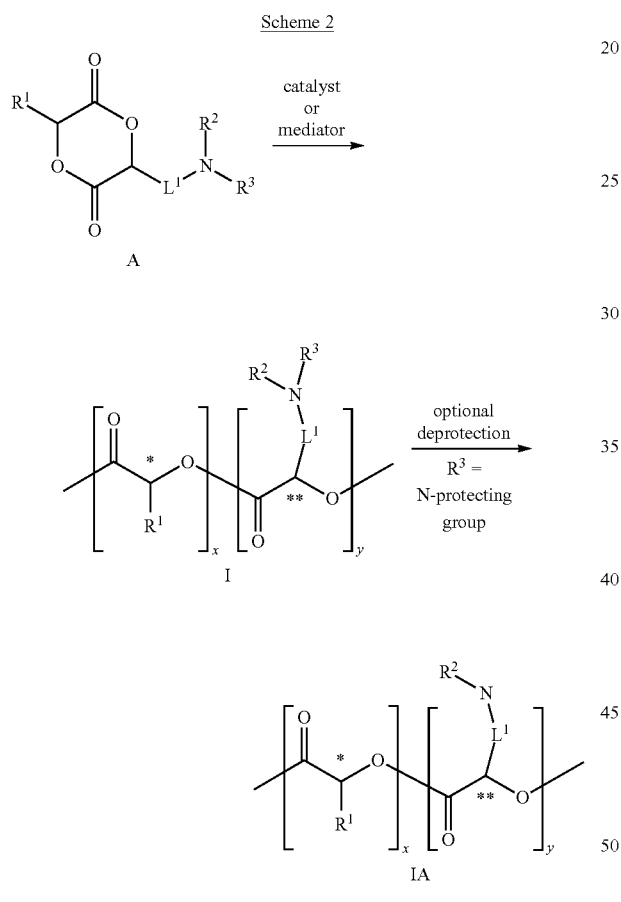

Pharmaceutically acceptable salts of any of the compounds described in Scheme 2 (e.g., a salt of any one of formulas A, I, and IA) are also encompassed by and can be used in this exemplary synthesis.

$R^1$, $L^1$, $R^2$, $R^3$, x, and y are each independently as described for any embodiment provided herein.

Other exemplary cyclic amide and cyclic ester compounds suitable for the ROP syntheses described herein include those described in US2013/0158021, US20150376144, and US2017/0246319, each of which is incorporated herein by reference. For example, exemplary cyclic compounds that can be used in the polymerization methods described herein are Compounds (3)-(11):

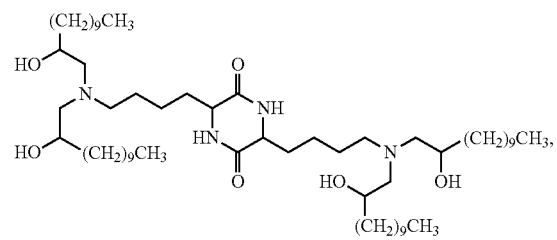

(3)

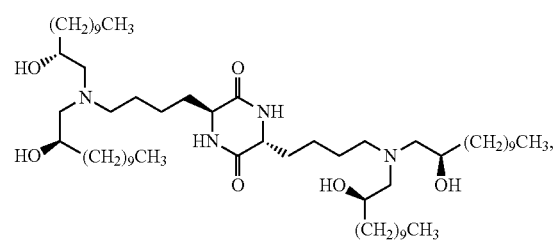

(4)

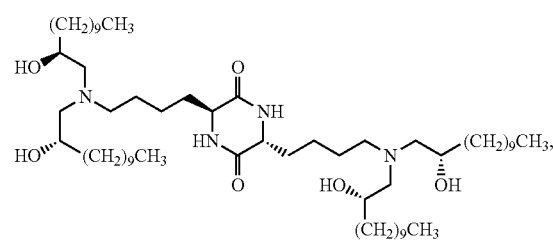

(5)

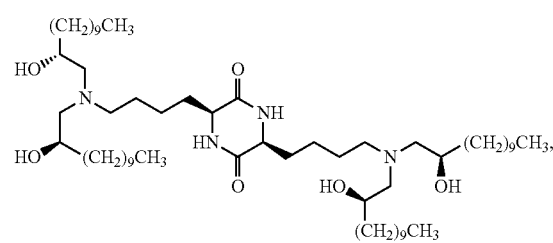

(6)

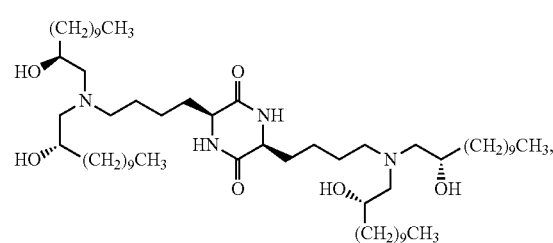

(7)

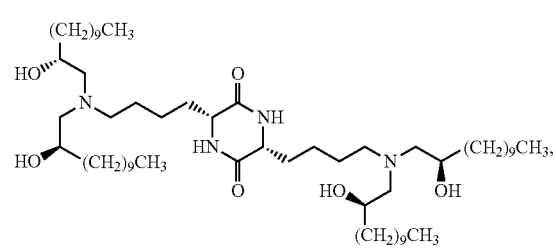

(8)

-continued

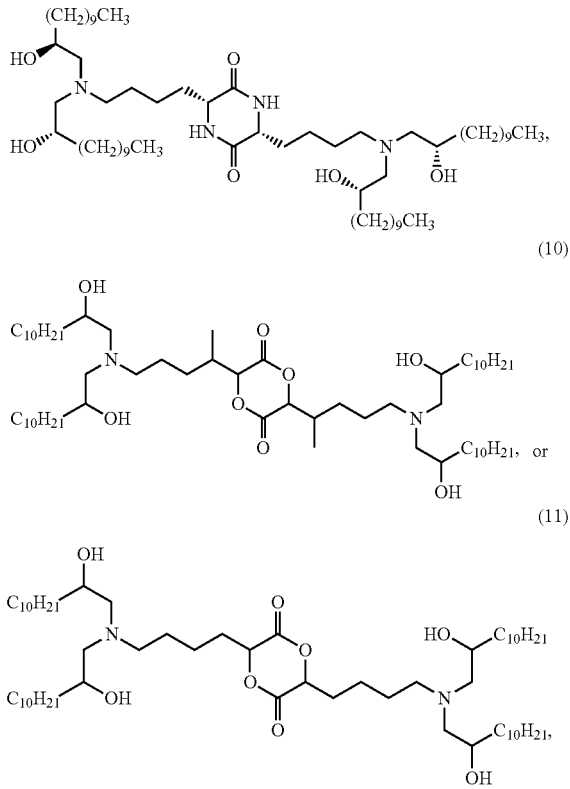

or a salt thereof.

Ring-opening polymerization (ROP) reactions can be mediated or catalyzed by metal compounds. Exemplary metal compounds that can act as a catalyst or mediator for polymerization include: Sn(II) compounds (e.g., Sn(2-ethylhexanoate)$_2$ (also referred to as Sn(octanoate)$_2$); aluminum alkoxides (including those formed in situ from AlEt$_3$ and an alcohol); and rare earth compounds. In embodiments, Sn(2-ethylhexanoate)$_2$ is used to effect the ROP reaction.

In embodiments, polymers described herein can be further processed or purified by recrystallization or precipitation from a mother liquor. Such recrystallizations or precipitations can be useful for the preparation of stereochemically enriched polymers.

Nucleic Acids

Synthesis of Nucleic Acids

Nucleic acids according to the present invention may be synthesized according to any known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, mutated T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7, mutated T7 or SP6 promoter, for in vitro transcription, followed by a desired nucleotide sequence that is a DNA reverse complementary sequence to a desired mRNA sequence, followed by a termination signal.

A desired mRNA sequence(s) according to the invention may be transcribed by incorporating into a DNA template the reverse complement of the desired mRNA sequence using standard methods. For example, starting from a desired amino acid sequence for an mRNA (e.g., an mRNA coding for an antigen, an enzyme, an antibody, an intrabody, an intracellularly acting protein, a cytosolic protein, a transmembrane protein, a membrane-bound protein, a secreted protein, a cell surface receptor or ligand, or a soluble receptor or ligand), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified Nucleic Acids

Modified nucleic acids according to the present invention may be include modifications and be prepared according to any known modifications and methods. For example, in some embodiments, mRNA according to the present invention may be synthesized as unmodified RNA or as modified RNA in accordance with known modifications and methods. Typically, RNAs are modified to enhance stability. Modifications of RNA can include, for example, modifications of the nucleotides of the RNA. A modified RNA such as modified mRNA (mmRNA) according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, modified RNAs such as mmRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, modified RNAs such as mmRNAs may contain sugar modifications. A typical sugar modification is a chemical modification of the sugar of the nucleotides it contains including, but not limited to, sugar modifications chosen from the group consisting of 4'-thioribonucleotide (see, e.g., US Patent Application Publication No. US 2016/0031928, incorporated by reference herein), 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, modified RNAs such as mmRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 20 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' —OH group is replaced with —OCH$_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{72'd}GpppG$, $m^{7,3'Ome}GpppG$, $m^{7,3'd}GpppG$ and their tetraphosphate derivatives) (see, e.g., Jemielity, J. et al., "*Novel 'anti-reverse' cap analogs with superior translational properties*", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G$ (5')ppp(5')N, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemiely, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-87 (2004)), phosphorothioate cap analogs (described in Grudzien-Nogalska, E., et al., RNA, 13: 1745-55 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-56). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Pharmaceutical Compositions

The present invention also provides compositions comprising a polymer as described herein for delivery of therapeutic agents.

Among other things, the present invention provides a pharmaceutical composition comprising a provided polymer and one or more therapeutic agents (e.g., nucleic acids). As described herein, such a polymer-based formulation for delivering therapeutic agents (e.g., nucleic acids) can provide one or more advantages. For example, such polymers can be beneficial in delivering nucleic acids, such as mRNA, for providing a therapeutic benefit such as producing encoded protein (where the nucleic acid is mRNA). Pharmaceutical compositions comprising a polymer described herein can also afford improved results in formulation processes (e.g., in preparing dry powder formulations).

In embodiments, a polymer and a therapeutic agent (e.g., one or more nucleic acids such as one or more mRNAs) are first mixed in a solution, e.g., an aqueous solution. Typically, the polymer and a therapeutic agent (e.g., one or more nucleic acids such as one or more mRNAs) form a complex when mixed. In embodiments, the polymer and a therapeutic agent (e.g., one or more nucleic acids such as one or more mRNAs) are complexed in a form of nanoparticles.

In embodiments, a polymer is mixed with a nanoparticle (e.g., a lipid nanoparticle comprising one or more lipids) that comprises a therapeutic agent (e.g., one or more nucleic acids such as one or more mRNAs). In embodiments, a lipid nanoparticle comprising a therapeutic agent can comprise one or more lipids that are cationic lipids, helper lipids (e.g., non-cationic lipids and/or cholesterol-based lipids), or PEG-modified lipids as described herein. In embodiments, a lipid nanoparticle comprising a therapeutic agent can comprise one or more lipids such as one or more cationic lipids, and/or one or more helper lipids (e.g., non-cationic lipids and/or cholesterol-based lipids), and/or PEG-modified lipids, and further comprises a polymer as described herein.

In embodiments, a composition is a pharmaceutical composition.

In embodiments, a composition (e.g., a pharmaceutical composition) comprises one or more nucleic acids. In embodiments, a composition (e.g., a pharmaceutical composition) comprises one or more mRNAs.

In embodiments, a composition (e.g., a nanoparticle) as described herein comprises any of the polymers described herein in an amount that is about 0.5% (w/w) to about 50% (w/w) of the combined dry weight of all lipids and polymer excipients in the composition (e.g., a lipid nanoparticle); e.g., about 0.5% (w/w) to about 20% (w/w). In embodiments, the polymer is present in an amount that is about 5% (w/w) to about 10% (w/w), about 5% (w/w) to about 15% (w/w), about 5% (w/w) to about 20% (w/w), about 5% (w/w) to about 25% (w/w), about 10% (w/w) to about 15% (w/w), about 10% (w/w) to about 20% (w/w), or about 10% (w/w) to about 25% (w/w).

Various sized nanoparticles may be formed according to the present invention. In various embodiments, a nanoparticle is characterized with an average diameter based on volume diameter using dynamic light scattering. In some embodiments, nanoparticles have an average diameter between about 50 nm and about 250 nm. In some embodiments, nanoparticles have an average diameter between about 50 nm and about 200 nm. In some embodiments, nanoparticles have an average diameter between about 75 nm and about 225 nm. In some embodiments, nanoparticles have an average diameter between about 100 nm and about 200 nm. In some embodiments, nanoparticles have an average diameter between about 125 nm and about 175 nm. In some embodiments, nanoparticles have an average diameter between about 140 nm and about 160 nm. In some embodiments, nanoparticles have an average diameter between about 50 nm and about 150 nm. In some embodiments, nanoparticles have an average diameter between about 75 nm and about 125 nm. In some embodiments, nanoparticles have an average diameter between about 50 nm and about 250 nm. In some embodiments, nanoparticles have an average diameter between about 90 nm and about 110 nm. In some embodiments, nanoparticles have an average diameter between about 150 nm and about 250 nm. In some embodiments, nanoparticles have an average diameter between about 175 nm and about 225 nm. In some embodiments, nanoparticles have an average diameter between about 190 nm and about 210 nm.

Nanoparticles may have a range of sizes in a mixture. Typically, the nanoparticles have a polydispersity index (PDI) of less than about 0.5 (e.g., less than about 0.45, 0.4, 0.35, 0.3, 0.25, 0.2, 0.15, or 0.1). In some embodiment, the nanoparticles have a PDI between about 0.1 and about 0.4. In some embodiments nanoparticles have a PDI between about 0.1 and about 0.4. In some embodiments nanoparticles have a PDI between about 0.1 and about 0.2. In some embodiments nanoparticles have a PDI between about 0.2 and about 0.3. In some embodiments, nanoparticles have a PDI between about 0.3 and about 0.4.

Nanoparticles may have a range of surface charges as measured through zeta potential measurements. In some embodiments, nanoparticles have a zeta potential between 0 and about 50 mV. In some embodiments nanoparticles have a zeta potential between about 5 and about 45 mV. In some embodiments nanoparticles have a zeta potential between about 10 and about 40 mV. In some embodiments nanoparticles have a zeta potential between about 10 and about 30 mV. In some embodiments nanoparticles have a zeta potential between about 20 and about 30 mV.

In some embodiments, a composition described herein is a lipid nanoparticle (e.g., a liposome) comprising one or more lipids. For example, lipid nanoparticles described herein can comprise cationic lipids, helper lipids (e.g., non-cationic lipids and/or cholesterol-based lipids), PEG-modified lipids, and/or polymers as described herein. As used herein, the term "liposome" refers to any lamellar, multilamellar, or solid lipid nanoparticle vesicle. Typically, a liposome as used herein can be formed by mixing one or more lipids or by mixing one or more lipids and polymer(s). Thus, the term "liposome" as used herein encompasses both lipid and polymer-based nanoparticles. Exemplary lipids are described herein.

In embodiments, a composition of the present invention is comprised of the polymer described previously, a lipid nanoparticle comprising one more polynucleotides, and one or more PEG-modified lipids. In embodiments, the composition comprises between about 0.5% and about 15% of one or more PEG-modified lipids. For example, in embodiments, the composition comprises between about 0.5% and about 14.5%, between about 0.5% and about 14%, between about 0.5% and about 13.5%, between about 0.5% and about 13%, between about 0.5% and about 12.5%, between about 0.5% and about 12%, between about 0.5% and about 12%, between about 0.5% and about 11.5%, between about 0.5% and about 11%, between about 0.5% and about 10.5%, between about 0.5% and about 10%, between about 0.5% and about 9.5%, between about 0.5% and about 9%, between about 0.5% and about 8.5%, between about 0.5% and about 8%, between about 0.5% and about 7.5%, between about 0.5% and about 7%, between about 1% and about 7%, between about 1.5% and about 7%, between about 2% and about 7%, between about 2.5% and about 7%, between about 3% and about 7%, between about 3.5% and about 7%, between about 4% and about 7%, between about 4.5% and about 7%, between about 5% and about 7%, between about 5.5% and about 7%, between about 6% and about 7%, or between about 6.5% and about 7% of one or more PEG modified lipids.

In embodiments, the composition comprises about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% of one or more PEG-modified lipids. In some embodiments, the composition comprises up to about 1%, up to about 2%, up to about 3%, up to about 4%, up to about 5%, up to about 6%, up to about 7%, up to about 8%, up to about 9%, or up to about 10% PEG-modified lipids. In embodiments, the composition comprises about 7% of one or more PEG-modified lipids. In embodiments, the PEG-modified lipid is DMG-PEG.

Cationic Lipids

As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]), WO 2012/170930 and WO 2013063468, each of which is incorporated herein by reference in its entirety. In certain embodiments, the compositions and methods of the invention employ a lipid nanoparticles comprising an ionizable cationic lipid described in International Patent Application No. PCT/US2013/034602, filed Mar. 29, 2013, Publ. No. WO 2013/149140 (incorporated herein by reference), such as, e.g., (15Z, 18Z)—N,N-dimethyl-6-(9Z, 12Z)-octadeca-9, 12-dien-1-yl)tetracosa-15,18-dien-1-amine (HGT5000), (15Z, 18Z)—N,N-dimethyl-6-((9Z, 12Z)-octadeca-9,12-dien-1-yl)tetracosa-4, 15,18-trien-1-amine (HGT5001), and (15Z,18Z)—N,N-dimethyl-6-((9Z, 12Z)-octadeca-9,12-dien-1-yl)tetracosa-5, 15, 18-trien-1-amine (HGT5002).

In some embodiments, a cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-l-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-l-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z,12Z)-octadeca-9, 1 2-dien-1-yl)-l,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D. V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, a cationic lipid may be chosen from XTC (2,2-Dilinoleyl-4-dimethylaminoethyl-[1,3]-dioxolane), MC3 (((6Z,9Z,28Z,31Z)-heptatriaconta-6,9,28, 31-tetraen-19-yl 4-(dimethylamino)butanoate), ALNY-100 ((3aR,5s,6aS)—N,N-dimethyl-2,2-di((9Z,12Z)-octadeca-9, 12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1, 16-diamide), DODAP (1,2-dioleyl-3-dimethylammonium propane), HGT4003 (WO 2012/170889, the teachings of which are incorporated herein by reference in their entirety), imidazole cholesterol ester lipid ("ICE") (WO 2011/068810, the teachings of which are incorporated herein by reference in their entirety), HGT5000 (international patent publication WO/2013/149140, the teachings of which are incorporated herein by reference in their entirety) or HGT5001 (cis or trans) (WO/2013/149140), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, a composition (e.g., a liposomal composition) comprises a further cationic lipid described in WO 2013/063468, filed Oct. 26, 2012 and in U.S. provisional application 61/953,516, filed Mar. 14, 2014, both of which are incorporated by reference herein.

In particular embodiments, a composition (e.g., a liposomal composition) comprises a further cationic lipid cKK-E12, or (3,6-bis(4-(bis(2-hydroxydodecyl)amino)butyl))piperazine-2,5-dione). The structure of cKK-E12 is shown below:

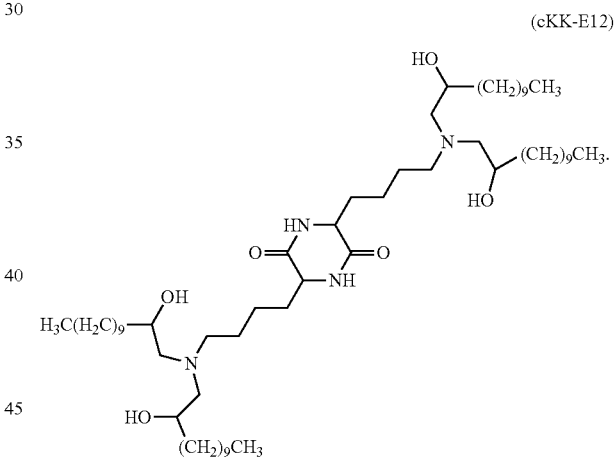

(cKK-E12)

In some embodiments, a further cationic lipid may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with a neutral lipid (e.g., dioleoylphosphatidyl-ethanolamine or "DOPE") or still other cationic or non-cationic lipids into a liposomal transfer vehicle or a lipid nanoparticle, and such liposomes can be used to enhance the delivery of nucleic acids into target cells. Other suitable further cationic lipids include, for example, 5-carboxyspermylglycinedioctadecylamide or "DOGS"; 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761); 1,2-dioleoyl-3-Dimethylammonium-Propane or "DODAP"; or 1,2-dioleoyl-3-trimethylammonium-propane or "DOTAP".

Additional exemplary further cationic lipids also include 1,2-distearyloxy-N,N-dimethyl-3-aminopropane or "DSDMA"; 1,2-dioleyloxy-N,N-dimethyl-3-aminopropane or "DODMA"; 1,2-dilinoleyloxy-N,N-dimethyl-3-aminopropane or "DLinDMA"; 1,2-dilinolenyloxy-N,N-dimethyl-3-aminopropane or "DLenDMA"; N-dioleyl-N,N-dimethyl-ammonium chloride or "DODAC"; N,N-distearyl-N,N-dimethylammonium bromide or "DDAB"; N-(1,2-dimyristyloxyprop-3-yl)-N,N-dimethyl-N-hydroxyethyl ammonium bromide or "DMRIE"; 3-dimethylamino-2-(cholest-5-en-3-beta-oxybutan-4-oxy)-1-(cis,cis-9,12-octadecadienoxy)propane or "CLinDMA"; 2-[5'-(cholest-5-en-3-beta-oxy)-3'-oxapentoxy)-3-dimethyl-1-(cis,cis-9',1-2'-octadecadienoxy)propane or "CpLinDMA"; N,N-dimethyl-3,4-dioleyloxybenzylamine or "DMOBA"; 1,2-N,N'-dioleylcarbamyl-3-dimethylaminopropane or "DOcarbDAP"; 2,3-dilinoleoyloxy-N,N-dimethylpropylamine or "DLinDAP"; 1,2-N,N'-Dilinoleylcarbamyl-3-dimethylaminopropane or "DLincarbDAP"; 1,2-dilinoleoylcarbamyl-3-dimethylaminopropane or "DLinCDAP"; 2,2-dilinoleyl-4-dimethylaminomethyl-[1,3]-dioxolane or "DLin-DMA"; 2,2-dilinoleyl-4-dimethylaminoethyl-[1,3]-dioxolane or "DLin-K-XTC2-DMA"; and 2-(2,2-di((9Z,12Z)-octadeca-9,1 2-dien-1-yl)-1,3-dioxolan-4-yl)-N,N-dimethyl-ethanamine (DLin-KC2-DMA)) (see WO 2010/042877; Semple et al., Nature Biotech. 28: 172-176 (2010)), or mixtures thereof. (Heyes, J., et al., J Controlled Release 107: 276-287 (2005); Morrissey, D. V., et al., Nat. Biotechnol. 23(8): 1003-1007 (2005); PCT Publication WO2005/121348A1). In some embodiments, one or more of the further cationic lipids comprise at least one of an imidazole, dialkylamino, or guanidinium moiety.

In some embodiments, the one or more further cationic lipids may be chosen from XTC (2,2-dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino) butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10, 13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of total cationic lipids in a composition (e.g., a liposomal composition) may be no more than 10%, no more than 20%, no more than 30%, no more than 40%, no more than 50%, no more than 60%, no more than 70%, no more than 80%, no more than 90%, or no more than 95% of total lipids as measured by molar ratios (mol %) or by weight (wt %).

In some embodiments, the percentage of total cationic lipids in a composition (e.g., a liposomal composition) may be greater than 10%, greater than 20%, greater than 30%, greater than 40%, greater than 50%, greater than 60%, greater than 70%, greater than 80%, greater than 90%, or greater than 95% of total lipids as measured by molar ratios (mol %) or by weight (wt %).

In some embodiments, total cationic lipid(s) constitute(s) about 30-50% (e.g., about 30-45%, about 30-40%, about 35-50%, about 35-45%, or about 35-40%) of the liposome by weight. In some embodiments, the cationic lipid constitutes about 30%, about 35%, about 40%, about 45%, or about 50% of a composition (e.g., a liposomal composition) by molar ratio. In some embodiments, total cationic lipid(s) constitute(s) about 30-50% (e.g., about 30-45%, about 30-40%, about 35-50%, about 35-45%, or about 35-40%) of the liposome by weight. In some embodiments, the cationic lipid constitutes about 30%, about 35%, about 40%, about 45%, or about 50% of a composition (e.g., a liposomal composition) by weight.

Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-l-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, I-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a composition. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

Suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744, 335), or imidazole cholesterol ester (ICE) (e.g., WO2011068810), which has the following structure,

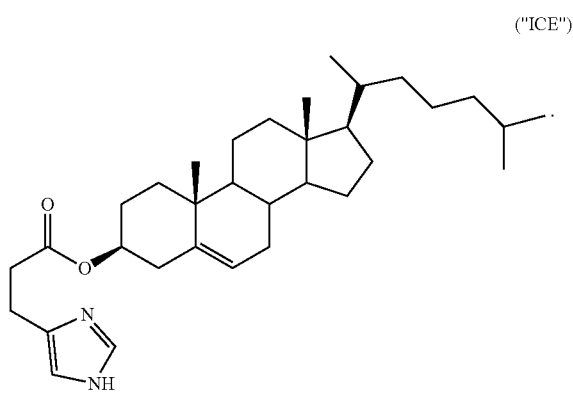 [SMILES: CC(C)CCCC(C)[C@H]1CCC2C3CC=C4C[C@@H](OC(=O)CCc5c[nH]cn5)CC[C@]4(C)C3CC[C@@]21C]

("ICE")

In some embodiments, a cholesterol-based lipid may comprise a molar ratio of about 2% to about 30%, or about 5% to about 20% of the total lipid present in a composition. In some embodiments, the percentage of cholesterol-based lipid in the lipid nanoparticle may be greater than 5, %, 10%, greater than 20%, greater than 30%, or greater than 40%.

In some embodiments, a cholesterol-based lipid may be present in a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEGylated Lipids

In embodiments, a PEGylated lipid is a polyethylene glycol (PEG)-modified phospholipid or a derivatized lipid such as derivatized ceramides (PEG-CER), including N-Octanoyl-Sphingosine-l-[Succinyl(Methoxy Polyethylene Glycol)-2000] (C8 PEG-2000 ceramide). Other contemplated PEG-modified lipids include, but are not limited to, a polyethylene glycol chain of up to 5 kDa in length covalently attached to a lipid with alkyl chain(s) of $C_6$-$C_{20}$ length. In embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-37), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome.

In embodiments, the PEG lipid is a methoxypoly(ethylene glycol) (mPEG) glyceride. In embodiments, the mPEG glyceride lipid is a diacylglycerol-PEG (DMG-PEG) (e.g., DMG-PEG2000, DMG-PEG5000). In embodiments, the mPEG glyceride lipid is a distearoylglycerol-PEG (DSG-PEG) (e.g., DSG-PEG2000, DSG-PEG5000). In embodiments, the DMG-PEG has the structure:

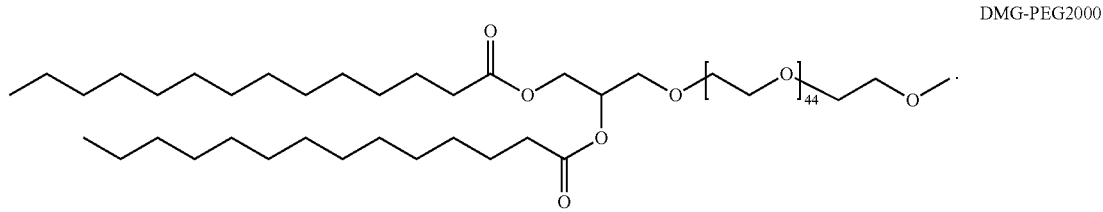

DMG-PEG2000

In embodiments, the DSG-PEG has the structure:

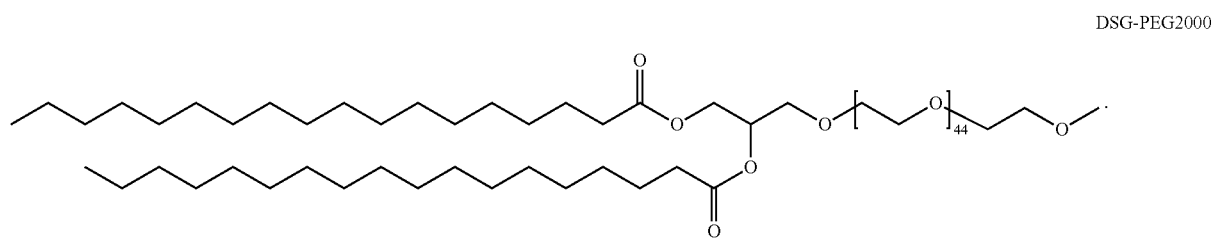

DSG-PEG2000

In embodiments, the PEG lipid is an mPEG ceramide. In embodiments, the mPEG ceramide lipid is $C_8$ PEG ceramide. In embodiments, the mPEG ceramide lipid is $C_{16}$ PEG ceramide. In embodiments, the $C_8$ PEG ceramide has the structure:

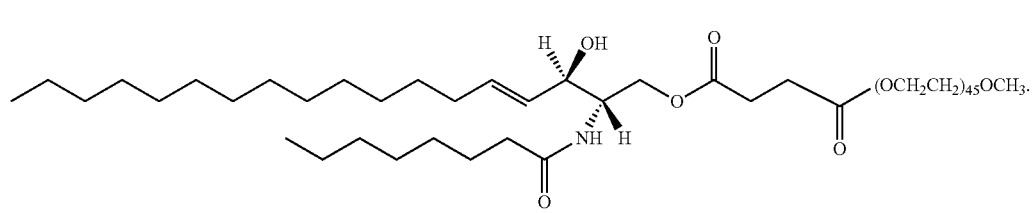

$C_8$ PEG ceramide

In embodiments, the $C_{16}$ PEG ceramide has the structure:

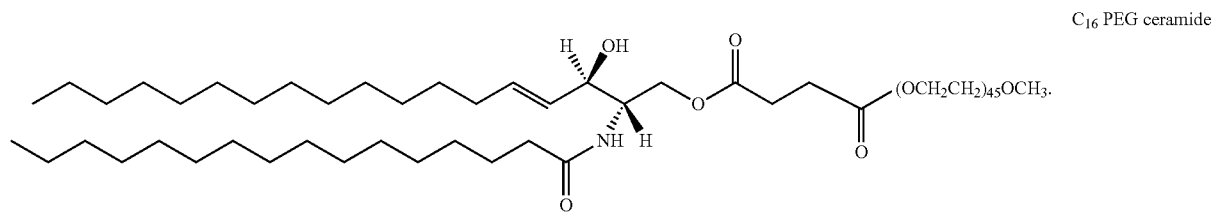

$C_{16}$ PEG ceramide

In embodiments, the PEG lipid is an mPEG phospholipid. In embodiments, the mPEG phospholipid is 1,2-Distearoyl-sn-glycero-3-phosphoethanolamine (DSPE)(18-0)-PEG. In embodiments, the mPEG phospholipid is 1,2-Dioleoyl-sn-Glycero-3-Phosphoethanolamine (DOPE)(18-1)-PEG. In embodiments, the mPEG phospholipid is 1,2-Ditetradecanoyl-sn-glycero-3-phosphoethanolamine (DMPE)(14-0)-PEG. In embodiments, the mPEG phospholipid is DPPE (16-0)-PEG. In embodiments, the DSPE(18-0)-PEG has the following structure:

Polymers

In some embodiments, a composition described herein includes another polymer, in combination with one or more lipids as described herein. Suitable other polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

Pharmaceutical Formulations and Therapeutic Uses

Polymers described herein may be used in the preparation of compositions (e.g., to construct liposomal compositions)

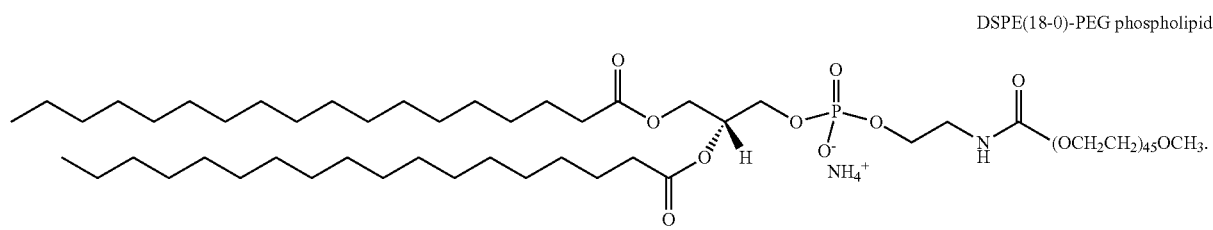

DSPE(18-0)-PEG phospholipid

According to various embodiments, the selection of cationic lipids, non-cationic lipids and/or PEG-modified lipids which comprise a lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly. In some embodiments, the percentage of PEG-modified lipid in a liposome may be greater than 1%, greater than 2%, greater than 5%, greater than 10%, or greater than 15%.

that facilitate or enhance the delivery and release of encapsulated materials (e.g., one or more therapeutic polynucleotides) to one or more target cells (e.g., by permeating or fusing with the lipid membranes of such target cells).

For example, when a liposomal composition (e.g., a lipid nanoparticle) comprises or is otherwise enriched with one or more of the compounds disclosed herein, the phase transition in the lipid bilayer of the one or more target cells may facilitate the delivery of the encapsulated materials (e.g., one or more therapeutic polynucleotides encapsulated in a lipid nanoparticle) into the one or more target cells.

Similarly, in certain embodiments polymers described herein may be used to prepare liposomal vehicles that are characterized by their reduced toxicity in vivo. In certain embodiments, the reduced toxicity is a function of the high transfection efficiencies associated with the compositions disclosed herein, such that a reduced quantity of such composition may administered to the subject to achieve a desired therapeutic response or outcome.

Thus, pharmaceutical formulations comprising a polymer described herein, nucleic acids, and optionally one or more PEG modified lipids provided by the present invention may be used for various therapeutic purposes. To facilitate delivery of nucleic acids in vivo, liposomal compositions described herein can be formulated in combination with one or more additional pharmaceutical carriers, targeting ligands or stabilizing reagents. In some embodiments, a polymer can be formulated via pre-mixed lipid solution. In other embodiments, a polymer can be formulated using post-insertion techniques into the lipid membrane of the nanoparticles. Techniques for formulation and administration of drugs may be found in "Remington's Pharmaceutical Sciences," Mack Publishing Co., Easton, Pa., latest edition.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the nucleic acids to a muscle cell. In some embodiments the administration results in delivery of the nucleic acids to a hepatocyte (i.e., liver cell).

Alternatively or additionally, pharmaceutical formulations of the invention may be administered in a local rather than systemic manner, for example, via injection of the pharmaceutical formulation directly into a targeted tissue, preferably in a sustained release formulation. Local delivery can be affected in various ways, depending on the tissue to be targeted. Exemplary tissues in which delivered mRNA may be delivered and/or expressed include, but are not limited to the liver, kidney, heart, spleen, serum, brain, skeletal muscle, lymph nodes, skin, and/or cerebrospinal fluid. In embodiments, the tissue to be targeted in the liver. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection.

Compositions described herein can comprise mRNA encoding polypeptides including those described herein (e.g., a polypeptide such as a protein).

In embodiments, a mRNA encodes a polypeptide.

In embodiments, a mRNA encodes a protein.

Exemplary polypeptides encoded by mRNA (e.g., exemplary proteins encoded by mRNA) are described herein.

The present invention provides methods for delivering a composition having full-length mRNA molecules encoding a peptide or protein of interest for use in the treatment of a subject, e.g., a human subject or a cell of a human subject or a cell that is treated and delivered to a human subject.

Accordingly, in certain embodiments the present invention provides a method for producing a therapeutic composition comprising full-length mRNA that encodes a peptide or protein for use in the delivery to or treatment of the lung of a subject or a lung cell. In certain embodiments the present invention provides a method for producing a therapeutic composition having full-length mRNA that encodes for cystic fibrosis transmembrane conductance regulator (CFTR) protein. In certain embodiments the present invention provides a method for producing a therapeutic composition having full-length mRNA that encodes for ATP-binding cassette sub-family A member 3 protein. In certain embodiments the present invention provides a method for producing a therapeutic composition having full-length mRNA that encodes for dynein axonemal intermediate chain 1 protein. In certain embodiments the present invention provides a method for producing a therapeutic composition having full-length mRNA that encodes for dynein axonemal heavy chain 5 (DNAH5) protein. In certain embodiments the present invention provides a method for producing a therapeutic composition having full-length mRNA that encodes for alpha-1-antitrypsin protein. In certain embodiments the present invention provides a method for producing a therapeutic composition having full-length mRNA that encodes for forkhead box P3 (FOXP3) protein. In certain embodiments the present invention provides a method for producing a therapeutic composition having full-length mRNA that encodes one or more surfactant protein, e.g., one or more of surfactant A protein, surfactant B protein, surfactant C protein, and surfactant D protein.

In certain embodiments the present invention provides a method for producing a therapeutic composition having full-length mRNA that encodes a peptide or protein for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition having full-length mRNA that encodes for a protein associated with a urea cycle disorder. In certain embodiments the present invention provides a method for producing a therapeutic composition having full-length mRNA that encodes for ornithine transcarbamylase (OTC) protein. In certain embodiments the present invention provides a method for producing a therapeutic composition having full-length mRNA that encodes for arginosuccinate synthetase 1 protein. In certain embodiments the present invention provides a method for producing a therapeutic composition having full-length mRNA that encodes for carbamoyl phosphate synthetase I protein. In certain embodiments the present invention provides a method for producing a therapeutic composition having full-length mRNA that encodes for arginosuccinate lyase protein. In certain embodiments the present invention provides a method for producing a therapeutic composition having full-length mRNA that encodes for arginase protein.

In certain embodiments the present invention provides a method for producing a therapeutic composition having full-length mRNA that encodes for a protein associated with a lysosomal storage disorder. In certain embodiments the present invention provides a method for producing a therapeutic composition having full-length mRNA that encodes for alpha galactosidase protein. In certain embodiments the present invention provides a method for producing a therapeutic composition having full-length mRNA that encodes for glucocerebrosidase protein. In certain embodiments the present invention provides a method for producing a therapeutic composition having full-length mRNA that encodes for iduronate-2-sulfatase protein. In certain embodiments the present invention provides a method for producing a therapeutic composition having full-length mRNA that encodes for iduronidase protein. In certain embodiments the present invention provides a method for producing a therapeutic composition having full-length mRNA that encodes for N-acetyl-alpha-D-glucosaminidase protein. In certain embodiments the present invention provides a method for producing a therapeutic composition having full-length mRNA that encodes for heparan N-sulfatase protein. In certain embodiments the present invention provides a method for producing a therapeutic composition having full-length mRNA that encodes for galactosamine-6 sulfatase protein. In certain embodiments the present invention provides a method for producing a therapeutic composition having full-length mRNA that encodes for beta-galactosidase protein. In certain embodiments the present invention provides a method for producing a therapeutic composition having full-length mRNA that encodes for lysosomal lipase protein. In certain embodiments the present invention provides a method for producing a therapeutic composition having full-length mRNA that encodes for arylsulfatase B (N-acetylgalactosamine-4-sulfatase) protein. In certain embodiments the present invention provides a method for producing a therapeutic composition having full-length mRNA that encodes for transcription factor EB (TFEB).

In certain embodiments the present invention provides a method for producing a therapeutic composition having full-length mRNA that encodes for a protein associated with a glycogen storage disorder. In certain embodiments the present invention provides a method for producing a therapeutic composition having full-length mRNA that encodes for acid alpha-glucosidase protein. In certain embodiments the present invention provides a method for producing a therapeutic composition having full-length mRNA that encodes for glucose-6-phosphatase (G6PC) protein. In certain embodiments the present invention provides a method for producing a therapeutic composition having full-length mRNA that encodes for liver glycogen phosphorylase protein. In certain embodiments the present invention provides a method for producing a therapeutic composition having full-length mRNA that encodes for muscle phosphoglycerate mutase protein. In certain embodiments the present invention provides a method for producing a therapeutic composition having full-length mRNA that encodes for glycogen debranching enzyme.

In certain embodiments the present invention provides a method for producing a therapeutic composition having full-length mRNA that encodes for a protein associated with amino acid metabolism. In certain embodiments the present invention provides a method for producing a therapeutic composition having full-length mRNA that encodes for phenylalanine hydroxylase enzyme. In certain embodiments the present invention provides a method for producing a therapeutic composition having full-length mRNA that encodes for glutaryl-CoA dehydrogenase enzyme. In certain embodiments the present invention provides a method for producing a therapeutic composition having full-length mRNA that encodes for propionyl-CoA carboxylase enzyme. In certain embodiments the present invention provides a method for producing a therapeutic composition having full-length mRNA that encodes for oxalase alanine-glyoxylate aminotransferase enzyme.

In certain embodiments the present invention provides a method for producing a therapeutic composition having full-length mRNA that encodes for a protein associated with a lipid metabolism or fibrotic disorder. In certain embodiments the present invention provides a method for producing a therapeutic composition having full-length mRNA that encodes for a mTOR inhibitor. In certain embodiments the present invention provides a method for producing a therapeutic composition having full-length mRNA that encodes for ATPase phospholipid transporting 8B1 (ATP8B1) protein. In certain embodiments the present invention provides a method for producing a therapeutic composition having full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition having full-length mRNA that encodes for PPAR-gamma protein or an active variant.

In certain embodiments, the present invention provides a method for producing a therapeutic composition having full-length mRNA that encodes for a protein associated with methylmalonic acidemia. For example, in certain embodiments the present invention provides a method for producing a therapeutic composition having full-length mRNA that encodes for methylmalonyl CoA mutase protein. In certain embodiments the present invention provides a method for producing a therapeutic composition having full-length mRNA that encodes for methylmalonyl CoA epimerase protein.

In certain embodiments the present invention provides a method for producing a therapeutic composition having full-length mRNA for which delivery to or treatment of the liver can provide therapeutic benefit. In certain embodiments the present invention provides a method for producing a therapeutic composition having full-length mRNA that encodes for ATP7B protein, also known as Wilson disease protein. In certain embodiments the present invention provides a method for producing a therapeutic composition having full-length mRNA that encodes for porphobilinogen deaminase enzyme. In certain embodiments the present invention provides a method for producing a therapeutic composition having full-length mRNA that encodes for one or clotting enzymes, such as Factor VIII, Factor IX, Factor VII, and Factor X. In certain embodiments the present invention provides a method for producing a therapeutic composition having full-length mRNA that encodes for human hemochromatosis (HFE) protein.

In certain embodiments the present invention provides a method for producing a therapeutic composition having full-length mRNA that encodes a peptide or protein for use in the delivery to or treatment of the cardiovasculature of a subject or a cardiovascular cell. In certain embodiments the present invention provides a method for producing a therapeutic composition having full-length mRNA that encodes for vascular endothelial growth factor A protein. In certain embodiments the present invention provides a method for producing a therapeutic composition having full-length mRNA that encodes for relaxin protein. In certain embodiments the present invention provides a method for producing a therapeutic composition having full-length mRNA that encodes for bone morphogenetic protein-9 protein. In certain embodiments the present invention provides a method for producing a therapeutic composition having full-length mRNA that encodes for bone morphogenetic protein-2 receptor protein.

In certain embodiments the present invention provides a method for producing a therapeutic composition having full-length mRNA that encodes a peptide or protein for use in the delivery to or treatment of the muscle of a subject or a muscle cell. In certain embodiments the present invention provides a method for producing a therapeutic composition having full-length mRNA that encodes for dystrophin protein. In certain embodiments the present invention provides a method for producing a therapeutic composition having full-length mRNA that encodes for frataxin protein. In certain embodiments the present invention provides a method for producing a therapeutic composition having full-length mRNA that encodes a peptide or protein for use in the delivery to or treatment of the cardiac muscle of a subject or a cardiac muscle cell. In certain embodiments the present invention provides a method for producing a therapeutic composition having full-length mRNA that encodes for a protein that modulates one or both of a potassium channel and a sodium channel in muscle tissue or in a muscle cell. In certain embodiments the present invention provides a method for producing a therapeutic composition having full-length mRNA that encodes for a protein that modulates a Kv7.1 channel in muscle tissue or in a muscle cell. In certain embodiments the present invention provides a method for producing a therapeutic composition having full-length mRNA that encodes for a protein that modulates a Nav1.5 channel in muscle tissue or in a muscle cell.

In certain embodiments the present invention provides a method for producing a therapeutic composition having full-length mRNA that encodes a peptide or protein for use in the delivery to or treatment of the nervous system of a subject or a nervous system cell. For example, in certain embodiments the present invention provides a method for producing a therapeutic composition having full-length mRNA that encodes for survival motor neuron 1 protein. For example, in certain embodiments the present invention provides a method for producing a therapeutic composition having full-length mRNA that encodes for survival motor neuron 2 protein. In certain embodiments the present invention provides a method for producing a therapeutic composition having full-length mRNA that encodes for frataxin protein. In certain embodiments the present invention provides a method for producing a therapeutic composition having full-length mRNA that encodes for ATP binding cassette subfamily D member 1 (ABCD1) protein. In certain embodiments the present invention provides a method for producing a therapeutic composition having full-length mRNA that encodes for CLN3 protein.

In certain embodiments the present invention provides a method for producing a therapeutic composition having full-length mRNA that encodes a peptide or protein for use in the delivery to or treatment of the blood or bone marrow of a subject or a blood or bone marrow cell. In certain embodiments the present invention provides a method for producing a therapeutic composition having full-length mRNA that encodes for beta globin protein. In certain embodiments the present invention provides a method for producing a therapeutic composition having full-length mRNA that encodes for Bruton's tyrosine kinase protein. In certain embodiments the present invention provides a method for producing a therapeutic composition having full-length mRNA that encodes for one or clotting enzymes, such as Factor VIII, Factor IX, Factor VII, and Factor X.

In certain embodiments the present invention provides a method for producing a therapeutic composition having full-length mRNA that encodes a peptide or protein for use in the delivery to or treatment of the kidney of a subject or a kidney cell. In certain embodiments the present invention provides a method for producing a therapeutic composition having full-length mRNA that encodes for collagen type IV alpha 5 chain (COL4A5) protein.

In certain embodiments the present invention provides a method for producing a therapeutic composition having full-length mRNA that encodes a peptide or protein for use in the delivery to or treatment of the eye of a subject or an eye cell. In certain embodiments the present invention provides a method for producing a therapeutic composition having full-length mRNA that encodes for ATP-binding cassette sub-family A member 4 (ABCA4) protein. In certain embodiments the present invention provides a method for producing a therapeutic composition having full-length mRNA that encodes for retinoschisin protein. In certain embodiments the present invention provides a method for producing a therapeutic composition having full-length mRNA that encodes for retinal pigment epithelium-specific 65 kDa (RPE65) protein. In certain embodiments the present invention provides a method for producing a therapeutic composition having full-length mRNA that encodes for centrosomal protein of 290 kDa (CEP290).

In certain embodiments the present invention provides a method for producing a therapeutic composition having full-length mRNA that encodes a peptide or protein for use in the delivery of or treatment with a vaccine for a subject or a cell of a subject. For example, in certain embodiments the present invention provides a method for producing a therapeutic composition having full-length mRNA that encodes for an antigen from an infectious agent, such as a virus. In certain embodiments the present invention provides a method for producing a therapeutic composition having full-length mRNA that encodes for an antigen from influenza virus. In certain embodiments the present invention provides a method for producing a therapeutic composition having full-length mRNA that encodes for an antigen from respiratory syncytial virus. In certain embodiments the present invention provides a method for producing a therapeutic composition having full-length mRNA that encodes for an antigen from rabies virus. In certain embodiments the present invention provides a method for producing a therapeutic composition having full-length mRNA that encodes for an antigen from cytomegalovirus. In certain embodiments the present invention provides a method for producing a therapeutic composition having full-length mRNA that encodes for an antigen from rotavirus. In certain embodiments the present invention provides a method for producing a therapeutic composition having full-length mRNA that encodes for an antigen from a hepatitis virus, such as hepatitis A virus, hepatitis B virus, or hepatitis C virus. In certain embodiments the present invention provides a method for producing a therapeutic composition having full-length mRNA that encodes for an antigen from human papillomavirus. In certain embodiments the present invention provides a method for producing a therapeutic composition having full-length mRNA that encodes for an antigen from a herpes simplex virus, such as herpes simplex virus 1 or herpes simplex virus 2. In certain embodiments the present invention provides a method for producing a therapeutic composition having full-length mRNA that encodes for an antigen from a human immunodeficiency virus, such as human immunodeficiency virus type 1 or human immunodeficiency virus type 2. In certain embodiments the present invention provides a method for producing a therapeutic composition having full-length mRNA that encodes for an antigen from a human metapneumovirus. In certain embodiments the present invention provides a method for producing a therapeutic composition having full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition having full-length mRNA that encodes for an antigen from malaria virus. In certain embodiments the present invention provides a method for producing a therapeutic composition having full-length mRNA that encodes for an antigen from zika virus. In certain embodiments the present invention provides a method for producing a therapeutic composition having full-length mRNA that encodes for an antigen from chikungunya virus.

In certain embodiments the present invention provides a method for producing a therapeutic composition having full-length mRNA that encodes for an antigen associated with a cancer of a subject or identified from a cancer cell of a subject. In certain embodiments the present invention provides a method for producing a therapeutic composition having full-length mRNA that encodes for an antigen determined from a subject's own cancer cell, i.e., to provide a personalized cancer vaccine. In certain embodiments the present invention provides a method for producing a therapeutic composition having full-length mRNA that encodes for an antigen expressed from a mutant KRAS gene.

In certain embodiments the present invention provides a method for producing a therapeutic composition having full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition having full-length mRNA that encodes for an antibody to OX40. In certain embodiments the present invention provides a method for producing a therapeutic composition having full-length mRNA that encodes for an antibody to VEGF. In certain embodiments the present invention provides a method for producing a therapeutic composition having full-length mRNA that encodes for an antibody to tissue necrosis factor alpha. In certain embodiments the present invention provides a method for producing a therapeutic composition having full-length mRNA that encodes for an antibody to CD3. In certain embodiments the present invention provides a method for producing a therapeutic composition having full-length mRNA that encodes for an antibody to CD19.

In certain embodiments the present invention provides a method for producing a therapeutic composition having full-length mRNA that encodes for an immunomodulator. In certain embodiments the present invention provides a method for producing a therapeutic composition having full-length mRNA that encodes for Interleukin 12. In certain embodiments the present invention provides a method for producing a therapeutic composition having full-length mRNA that encodes for Interleukin 23. In certain embodiments the present invention provides a method for producing a therapeutic composition having full-length mRNA that encodes for Interleukin 36 gamma. In certain embodiments the present invention provides a method for producing a therapeutic composition having full-length mRNA that encodes for a constitutively active variant of one or more stimulator of interferon genes (STING) proteins.

In certain embodiments the present invention provides a method for producing a therapeutic composition having full-length mRNA that encodes for an endonuclease. In certain embodiments the present invention provides a method for producing a therapeutic composition having full-length mRNA that encodes for an RNA-guided DNA endonuclease protein, such as Cas 9 protein. In certain embodiments the present invention provides a method for producing a therapeutic composition having full-length mRNA that encodes for a meganuclease protein. In certain embodiments the present invention provides a method for producing a therapeutic composition having full-length mRNA that encodes for a transcription activator-like effector nuclease protein. In certain embodiments the present invention provides a method for producing a therapeutic composition having full-length mRNA that encodes for a zinc finger nuclease protein.

In embodiments, exemplary therapeutic uses result from the delivery of mRNA encoding a secreted protein. Accordingly, in embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof) along with other components set out herein, and methods of the invention may comprise preparing and/or administering a composition comprising an mRNA encoding a protein listed in Table 1 (or a homolog thereof) along with other components set out herein.

TABLE 1

| Uniprot ID | Protein Name | Gene Name |
|---|---|---|
| | Secreted Proteins | |
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |

TABLE 1-continued

Secreted Proteins

| Uniprot ID | Protein Name | Gene Name |
|---|---|---|
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (S. cerevisiae), isoform CRA_a | SEC11L3 |
| B4DJF9 | Protein Wnt | WNT4 |
| B4DUL4 | SEC11-like 1 (S. cerevisiae), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |

TABLE 1-continued

Secreted Proteins

| Uniprot ID | Protein Name | Gene Name |
|---|---|---|
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |

TABLE 1-continued

Secreted Proteins

| Uniprot ID | Protein Name | Gene Name |
|---|---|---|
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |

TABLE 1-continued

Secreted Proteins

| Uniprot ID | Protein Name | Gene Name |
| --- | --- | --- |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |

TABLE 1-continued

Secreted Proteins

| Uniprot ID | Protein Name | Gene Name |
| --- | --- | --- |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |

TABLE 1-continued

Secreted Proteins

| Uniprot ID | Protein Name | Gene Name |
|---|---|---|
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |

TABLE 1-continued

Secreted Proteins

| Uniprot ID | Protein Name | Gene Name |
|---|---|---|
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |

TABLE 1-continued

Secreted Proteins

| Uniprot ID | Protein Name | Gene Name |
|---|---|---|
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |

TABLE 1-continued

Secreted Proteins

| Uniprot ID | Protein Name | Gene Name |
|---|---|---|
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |

TABLE 1-continued

Secreted Proteins

| Uniprot ID | Protein Name | Gene Name |
|---|---|---|
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |

TABLE 1-continued

Secreted Proteins

| Uniprot ID | Protein Name | Gene Name |
| --- | --- | --- |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |

TABLE 1-continued

Secreted Proteins

| Uniprot ID | Protein Name | Gene Name |
|---|---|---|
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |

TABLE 1-continued

Secreted Proteins

| Uniprot ID | Protein Name | Gene Name |
|---|---|---|
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1(XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |

TABLE 1-continued

Secreted Proteins

| Uniprot ID | Protein Name | Gene Name |
|---|---|---|
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |

TABLE 1-continued

Secreted Proteins

| Uniprot ID | Protein Name | Gene Name |
|---|---|---|
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |

TABLE 1-continued

Secreted Proteins

| Uniprot ID | Protein Name | Gene Name |
|---|---|---|
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable Carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |

TABLE 1-continued

Secreted Proteins

| Uniprot ID | Protein Name | Gene Name |
|---|---|---|
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroactherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |

TABLE 1-continued

Secreted Proteins

| Uniprot ID | Protein Name | Gene Name |
|---|---|---|
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q76510 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |

TABLE 1-continued

Secreted Proteins

| Uniprot ID | Protein Name | Gene Name |
|---|---|---|
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |

TABLE 1-continued

Secreted Proteins

| Uniprot ID | Protein Name | Gene Name |
|---|---|---|
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |

TABLE 1-continued

Secreted Proteins

| Uniprot ID | Protein Name | Gene Name |
|---|---|---|
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |

TABLE 1-continued

Secreted Proteins

| Uniprot ID | Protein Name | Gene Name |
|---|---|---|
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orf39 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |

TABLE 1-continued

Secreted Proteins

| Uniprot ID | Protein Name | Gene Name |
|---|---|---|
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |

TABLE 1-continued

Secreted Proteins

| Uniprot ID | Protein Name | Gene Name |
| --- | --- | --- |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |

TABLE 1-continued

Secreted Proteins

| Uniprot ID | Protein Name | Gene Name |
| --- | --- | --- |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |

TABLE 1-continued

Secreted Proteins

| Uniprot ID | Protein Name | Gene Name |
|---|---|---|
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof) along with other components set out herein, and methods of the invention may comprise preparing and/or administering a composition comprising an mRNA encoding a protein chosen from the proteins listed in Table 2 (or a homolog thereof) along with other components set out herein.

TABLE 2

Additional Exemplary Proteins

| Uniprot ID | Protein Name | Gene Name |
|---|---|---|
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC116 | SEC11B |
| P0C854 | Putative cat eye syndrome critical region protein 9 | CECR9 |

TABLE 2-continued

Additional Exemplary Proteins

| Uniprot ID | Protein Name | Gene Name |
|---|---|---|
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 1 and Table 2 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1 and Table 2; thus, compositions of the invention may comprise an mRNA encoding a protein chosen from mammalian homologs or homologs from an animal of veterinary or industrial interest of a protein listed in Table 1 and Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 1 and Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a lysosomal protein chosen from Table 3. In some embodiments, the compositions and methods of the invention provide for the delivery of one or more mRNAs encoding one or more lysosomal and/or related proteins listed in Table 3; thus, compositions of the invention may comprise an mRNA encoding a protein listed in Table 3 (or a homolog thereof) along with other components set out herein, and methods of the invention may comprise preparing and/or administering a composition comprising an mRNA encoding a protein chosen from the proteins listed in Table 3 (or a homolog thereof) along with other components set out herein.

TABLE 3

Lysosomal and Related Proteins

α-fucosidase
α-galactosidase
α-glucosidase
α-Iduronidase
α-mannosidase
α-N-acetylgalactosaminidase (α-galactosidase B)
β-galactosidase
β-glucuronidase
β-hexosaminidase
β-mannosidase
3-hydroxy-3-methylglutaryl-CoA (HMG-CoA) lyase
3-methylcrotonyl-CoA carboxylase
3-O-sulfogalactosyl cerebroside sulfatase (arylsulfatase A)
acetyl-CoA transferase
acid alpha-glucosidase
acid ceramidase
acid lipase
acid phosphatase
acid sphingomyelinase
alpha-galactosidase A
arylsulfatase A
beta-galactosidase
beta-glucocerebrosidase
beta-hexosaminidase
Biotinidase
cathepsin A
cathepsin K
CLN3
CLN5
CLN6
CLN8
CLN9
cystine transporter (cystinosin)
cytosolic protein beta3A subunit of the adaptor protein-3 complex, AP3
formyl-Glycine generating enzyme (FGE)
Galactocerebrosidase
galactose-1-phosphate uridyltransferase (GALT)
galactose 6-sulfate sulfatase (also known as N-acetylgalactosamine-6-sulfatase)
Glucocerebrosidase
glucuronate sulfatase
glucuronidase
glycoprotein cleaving enzymes
glycosaminoglycan cleaving enzymes
glycosylasparaginase (aspartylglucosaminidase)
GM2-AP
Heparan-alpha-glucosaminide N-acetyltransferase (HGSNAT, TMEM76)
Heparan sulfatase
hexosaminidase A lysosomal proteases methylmalonyl-CoA mutase
Hyaluronidase
Iduronate sulfatase
LAMP-2
lysosomal α-mannosidase
Lysosomal p40 (C2orf18)
Major facilitator superfamily domain containing 8 protein (MFSD8 or CLN7)
N-acetylgalactosamine 4-sulfatase
N-acetyl glucosamine 6-sulfatase
N-acetyl glucosaminidase
N-acetylglucosamine-1-phosphate transferase
NPC1
NPC2
palmitoyl-protein thioesterase
palmitoyl-protein thioesterase (CLN1)
Saposin A (Sphingolipid activator protein A)
Saposin B (Sphingolipid activator protein B)
Saposin C (Sphingolipid activator protein C)
Saposin D (Sphingolipid activator protein D)
sialic acid transporter (sialin)
Sialidase
Sialin
Sulfatase
Transmembrane protein 74 (TMEM74)
tripeptidyl-peptidase
tripeptidyl-peptidase I (CLN2)
UDP-N-acetylglucosamine-phosphotransferase Information regarding lysosomal proteins is available from Lubke et al., "Proteomics of the Lysosome," *Biochim Biophys Acta.* (2009) 1793: 625-35. In some embodiments, the protein listed in Table 3 and encoded by mRNA in the compositions and methods of the invention is a human protein. Sequences of the listed proteins are also available for various animals, including various mammals and animals of veterinary or industrial interest as described above.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

TABLE 4

Exemplary Indications and Related Proteins

| Indication | Therapeutic Protein |
| --- | --- |
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |
| Acute intermittent porphyria | Porphobilinogen deaminase |
| Acute lymphocytic leukemia | |
| Acute myeloid leukemia | |
| Addison's disease | |
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |

TABLE 4-continued

Exemplary Indications and Related Proteins

| Indication | Therapeutic Protein |
| --- | --- |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |
| Classic Rett Syndrome | |
| Classical galactosemia | Galactose-1-phosphate uridylyltransferase |
| Clostridium difficile associated diarrhea | |
| Clotting disorders | |
| COAD/COPD | |
| Cocaine addiction | |
| COL4A5-related disorders | |
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |

TABLE 4-continued

Exemplary Indications and Related Proteins

| Indication | Therapeutic Protein |
|---|---|
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |
| Glioblastoma multiforme | |
| Glomerulonephritis | |
| Glutaric acidemia, type I | Glutaryl-CoA dehydrogenase |
| GM2 gangliosidosis | HEXA, HEXB |
| Gout | Urate oxidase |
| Graft versus host disease | |
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |

TABLE 4-continued

Exemplary Indications and Related Proteins

| Indication | Therapeutic Protein |
|---|---|
| Hemophilia B | Factor IX |
| Hepatitis B, Hepatitis C | Interferon alpha |
| HER2+ breast cancer, gastric cancer | Anti-HER2 mAb |
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (Clostridium difficile prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |
| Long-chain 3-OH acyl-CoA dehydrogenase deficiency | Long-chain-3-hydroxyacyl-CoA dehydrogenase |
| Lower respiratory infections | |

TABLE 4-continued

Exemplary Indications and Related Proteins

| Indication | Therapeutic Protein |
|---|---|
| Lysosomal acid lipase deficiency | Lysosomal acid lipase |
| Macular degeneration | |
| Major depressive disorder | |
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| Pediculosis capitis (head lice) | |
| Pelizaeus-Merzbacher disease | |
| Pemphigus vulgaris | |
| Peptic ulcer disease | |

TABLE 4-continued

Exemplary Indications and Related Proteins

| Indication | Therapeutic Protein |
|---|---|
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |
| Pompe disease | Alpha glucosidase |
| Porphyria cutanea tarda | Uroporphyrinogen decarboxylase |
| Post herpetic neuralgia | |
| Post-organ transplant | |
| Pouchitis | |
| PPM-X Syndrome | |
| Prader-Willi syndrome | |
| Preeclampsia | |
| Premature ejaculation | |
| Prematurity and low birth weight | |
| Primary ciliary dyskinesia | DNAH5, DNAI1 |
| Primary glomerular diseases | |
| Primary humoral immune deficiencies (e.g., CVID) | Immunoglobulin |
| Proctitis | |
| Progressive familial intrahepatic cholestasis (PFIC) | FIC1, BSEP, MDR3 |
| Progressive multifocal leukoencephalopathy | |
| Progressive supranuclear palsy | |
| Propionic acidemia | Propionyl-CoA carboxylase |
| Prostate cancer | |
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |

TABLE 4-continued

Exemplary Indications and Related Proteins

| Indication | Therapeutic Protein |
|---|---|
| Surfactant deficiency | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, the present invention is used to prevent, treat and/or cure a subject affected with a disease or disorder listed or associated with the proteins listed in Tables 1, 2, 3, or 4. In some embodiments, an mRNA encodes one or more of Cystic Fibrosis Transmembrane Conductance Regulator (CFTR), argininosuccinate synthetase (ASS1), Factor IX, survival motor neuron 1 (SMN1), or phenylalanine hydroxylase (PAH).

While certain compounds, compositions and methods of the present invention have been described with specificity in accordance with certain embodiments, the following examples serve only to illustrate the compounds of the invention and are not intended to limit the same.

EXAMPLES

Synthesis of PCMMA Monomers and Copolymers

An exemplary polymer synthesis is described in Scheme 3.

Scheme 3

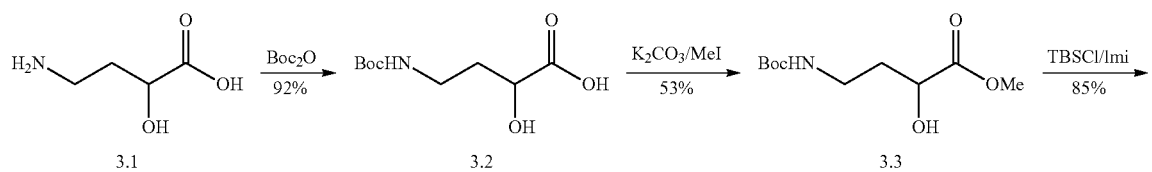

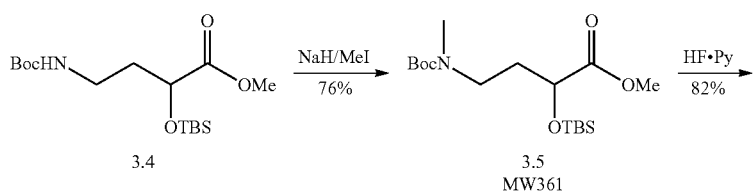

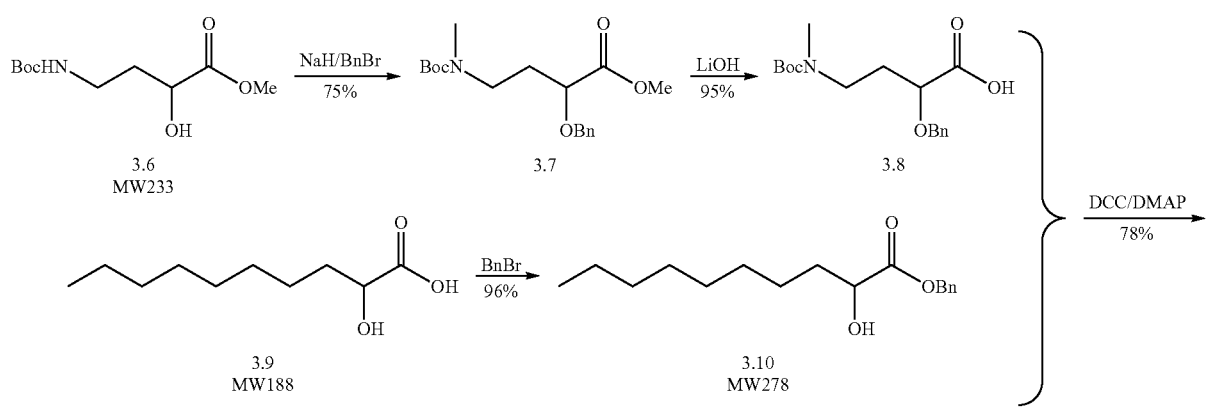

123

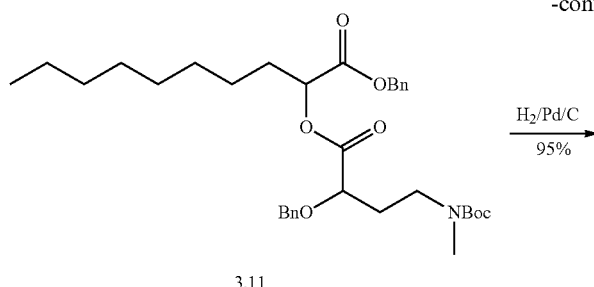

3.11

124

-continued

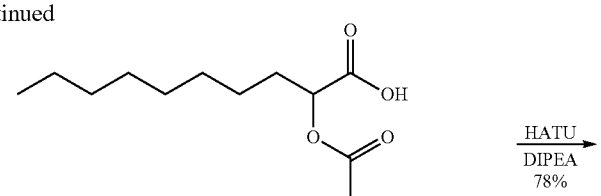

3.12

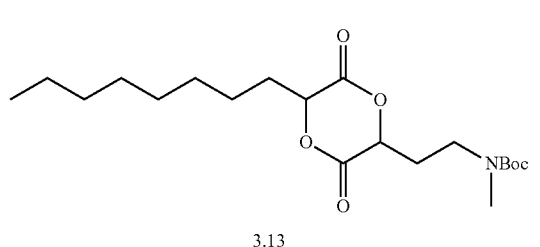

3.13

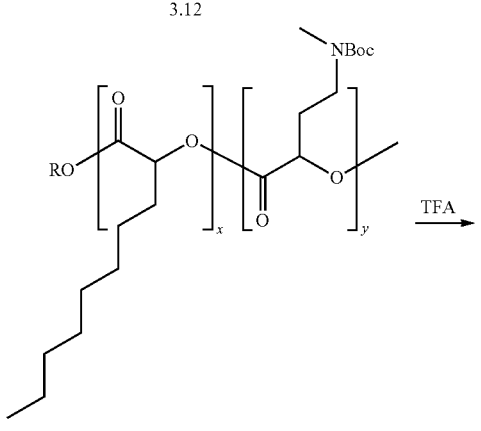

PCMMA-BOC
(Capric)

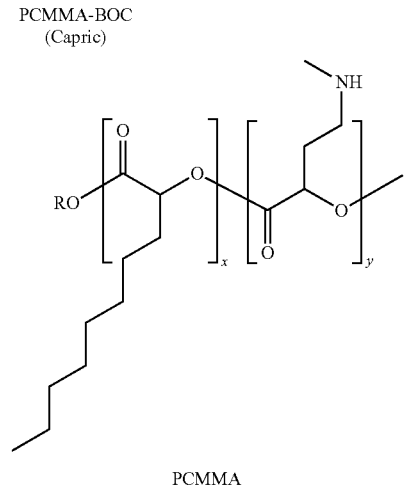

PCMMA
(Capric)

Example 1. Synthesis of Compound 3.13 (PCMMA Monomer)

Synthesis of 3.2

To a solution of 3.1 (25 g, 210 mmol) and $K_2CO_3$ (83 g, 601 mmol) in water (125 mL) cooled in ice-water bath was dropped in a solution of di-tert-butyl dicarbonate (50 g, 229 mmol) in 1,4-dioxane (80 mL). After the addition was complete, the reaction mixture was allowed to slowly attain room temperature and was stirred for 48 h. The reaction mixture was extracted with diethyl ether (70 mL×2). The aqueous layer was acidified with 6N HCl to pH=4 and then extracted with ethyl acetate (600 mL×4). The combined organic extracts were washed with brine (800 mL), dried over $Na_2SO_4$ and filtered. The filtrate was evaporated to give 42.5 g (92%) of product 3.2 as slightly yellow oil.

Synthesis of 3.3

To a stirred mixture of 3.2 (30 g, 137 mmol) and $K_2CO_3$ (56.7 g, 411 mmol) in DMF (200 mL) at room temperature was added methyl iodide (25.6 mL, 4.11 mmol) through a syringe. The resulting mixture was stirred at room temperature under nitrogen for 48 h. To the reaction system was added ethyl acetate (1000 mL) and water (500 ml). The mixture was then neutralized with 6 N HCl and extracted with ethyl acetate (1000 mL×3). All the organic extracts were combined, washed with brine (1000 ml), dried over $Na_2SO_4$, and filtered. The filtrate was evaporated in vacuo and the residue was purified by silica gel column (330 g) on an ISCO (automatic chromatography system) eluting with 0-50% EtOAc in hexanes to give 17 g of 3.3 (53%) as a colorless oil.

Synthesis of 3.4

The starting compound 3.3 (17 g, 73 mmol) was dissolved in anhydrous dichloromethane (100 ml). To this solution was added DMAP (1.2 g, 10 mmol), imidazole (10 g, 146 mmol) and a solution of TBDMSCl (22 g, 146 mmol) in anhydrous dichloromethane (20 ml). The resulting solution was then stirred at room temperature overnight. The reaction mixture was filtered and washed by dichloromethane. All the filtrates were combined and evaporated in vacuo. The residue was purified by silica gel column chromatography (330 g) on an ISCO eluting with 0-50% EtOAc in hexanes to give 21.6 g of 3.4 (85%) as a colorless oil.

Synthesis of 3.5

To a solution of 3.4 (21.6 g, 62 mmol) in DMF (125 mL) cooled in an ice-water bath was added portion-wise sodium hydride (4.9 g, 123 mmol, 60%) under a flow of nitrogen. Methyl iodide (39 mL, 620 mmol) was then added via a syringe. After complete addition, the reaction mixture was warmed up slowly to room temperature and was stirred for 2.5 h. The reaction mixture was mixed with ethyl acetate (500 mL) and slowly poured into a saturated aqueous $NH_4Cl$ solution to adjust the pH to 7. The resulting solution was extracted with ethyl acetate (600 mL×2). The combined organic extracts were washed with brine (400 ml), dried over $Na_2SO_4$ and filtered. The filtrate was evaporated in vacuo and the residue was purified by silica gel column (330 g) on an ISCO eluting with 0-60% EtOAc in hexanes to give 17 g of 3.5 (76%) as a colorless oil.

Synthesis of 3.6

To a solution of 3.5 (17.0 g, 2.36 mmol) in THF (anhydrous, 220 mL) in 500 ml Teflon flask at 0° C. was added dropwisely a 70% wt/30% wt HF-pyridine solution (22 mL, 848 mmol). The resulting mixture was stirred at room temperature for 40 h. The reaction solution was diluted with DCM (50 mL) and carefully neutralized with 10% NaOH aqueous solution and $Na_2CO_3$ saturated aqueous solution. The DCM layer was separated. The aqueous layer was extracted with DCM (150 mL). The combined organic phase was dried over $Na_2SO_4$ and evaporated. The light yellow oily residue (15 g) was purified by silica gel column (220 g) on an ISCO eluting with 0-60% EtOAc in hexanes to give 9.6 g of 3.6 (82%) as a colorless oil.

Synthesis of 3.7

To a solution of 3.6 (9.6 g, 38.9 mmol) in anhydrous THF (100 mL) that was cooled in an ice-water bath was added portion-wise sodium hydride (1.7 g, 42.8 mmol, 60%) under a flow of nitrogen. Once gas evolution ceased, tetrabutylammonium iodide (0.36 g, 1 mmol) was added, followed by the addition of benzyl bromide (5.1 mL, 42.8 mmol) via a syringe. After complete addition, the reaction mixture was warmed up slowly to room temperature and stirred overnight. The reaction mixture was slowly poured into a saturated aqueous $NH_4Cl$ solution to adjust pH to 7. The resulting solution was extracted with chloroform (500 mL×2). The combined organic extracts were dried over $Na_2SO_4$ and filtered. The filtrate was evaporated in vacuo and the residue was purified by silica gel column chromatography (330 g) on an ISCO eluting with 0-50% EtOAc in hexanes to give 9.8 g of 3.7 (75%) as a colorless oil.

Synthesis of 3.8

To a solution of compound 3.7 (9.8 g, 29 mmol) in 1,4-dioxane (70 mL) that was cooled in an ice-water bath was added dropwise a solution of lithium hydroxide (2.43 g, 58 mmol) in water (30 ml). The resulting mixture was warmed up slowly to room temperature and then stirred overnight. While cooling in ice-water bath, the reaction mixture was then acidified with 1 N HCl (40 mL) to pH=4 and then extracted with chloroform (300 mL×3). The combined organic extracts were washed with brine (200 ml), dried over $Na_2SO_4$ and filtered. The filtrate was evaporated to give 8.9 g (95%) of product 3.8 as slightly yellow oil.

Synthesis of 3.10

The starting compound 3.9 (5 g, 26.6 mmol) was dissolved in ethyl acetate (125 ml). To this solution was added benzyl bromide (5.1 mL, 42.8 mmol), triethylamine (11.9 mL, 79.8 mmol), and tetrabutylammonium iodide (15.6 g, 42.8 mmol). The resulting solution was stirred at 75° C. under a nitrogen atmosphere for 48 h. The reaction mixture was filtered through Celite and washed with ethyl acetate. The filtrates were combined and evaporated in vacuo. The residue was purified by silica gel column chromatography (330 g) on an ISCO eluting with 0-30% EtOAc in hexanes to give 7 g of 3.10 (96%) as a colorless oil.

Synthesis of 3.11

To a solution of compound 3.8 (7.68 g, 23.8 mmol) in DCM (200 ml) was added DMAP (8.3 g, 68 mmol) and a solution of compound 3.10 (2.6.3 g, 22.66 mmol) in DCM (50 ml). The resulting solution was cooled in an ice-water bath and DCC (18.8 g, 90 mmol) was then added. The mixture was allowed to warm to 40° C. and stirred for 3.5 days. The reaction mixture was filtered through Celite and washed with DCM. All the filtrates were combined and solvent was removed under reduced pressure. The residue was taken up in $Et_2O$ and filtered. The filtrate was evaporated in vacuo and the residue was purified by silica gel column (330 g) on ISCO automatic chromatography system eluting with 0-30% EtOAc in hexane to give 10.3 g (78%) of the desired product 3.11 as colorless oil.

Synthesis of 3.12

A mixture of 3.11 (5.0 g, 8.6 mmol) and 10% Pd/C (2.3 g) in EtOAc (150 ml) was stirred at room temperature under a hydrogen balloon for 65 h. It was then filtered through Celite. The Celite was rinsed with EtOAc (150 mL×3). The combined filtrate was evaporated to give 3.3 g of 3.12 (95%) as a slightly yellow oil.

Synthesis of 3.13

To a solution of 3.12 (3.3 g, 8.2 mmol) in a mixture of DCM (anhydrous, 80 ml) and $CH_3CN$ (anhydrous, 160 ml) was added DIPEA (4 mL, 23 mmol), followed by HATU (4.7 g, 12 mmol). The resulting mixture was stirred at room temperature under $N_2$ for 1.5 h. Volatiles were removed under reduced pressure. The residue was extracted with hexane/diethyl ether (1:2,300 mL×3). All the extracts were combined and evaporated to give 3.3 g of a light red-brown oil, which was then mixed with hexane/diethyl ether (10:1, 200 mL). Filtration and concentration gave 3.1 g of crude product that was further purified by silica gel column chromatography (330 g) on an ISCO eluting with 0-50% EtOAc in hexanes to give 2.45 g of 3.13 (78%) as a colorless oil.

Example 2. Synthesis of PCMMA-Boc Copolymers

Synthesis of PCMMA-BOC

To a solution of 3.13 (300 mg, 0.78 mmol) in anhydrous DCM (1 mL) and anhydrous benzene (2 mL) in an oven-dried Schlenk tube equipped with a magnetic stirring bar under nitrogen atmosphere was added a 0.1 M solution of Sn(2-ethylhexanoate)$_2$ in anhydrous benzene (13 µL, 0.0039 mmol) and 0.1 M solution of 4-tert-butylbenzyl alcohol in anhydrous benzene (13 µL, 0.0039 mmol). The resulting solution was degassed three times using Freeze-Pump-Thaw method. The solvents were removed under reduced pressure. The Schlenk tube was filled with nitrogen, sealed and immersed in an oil bath (110° C.). After stirring for 72 h at 110° C., the reaction mixture was cooled to room temperature and dissolved in anhydrous dichloromethane. The result dichloromethane solution was concentrated in vacuo to give 289 mg of crude copolymer (WSM-641-123C). The crude polymer was dissolved in 1,2-dichloroethane and loaded onto Sephadex LH-20 column and eluted with 1,2-dichloroethane. Fractions containing product were combined and concentrated in vacuo to yield 271 mg of Target PCMMA-BOC as a colorless oil.

Polymers prepared herein can be characterized by various methods known in the art, including gel permeation chromatograph (GPC). For example, the molecular weight of a polymer can be described by Mp (peak molecular weight), Mn (number-average molecular weight), Mw (weight-average molecular weight), Mz (Z-average molecular weight), and PDI (polydispersity as calculated by the ration of Mw/Mn).

Table 5 provides GPC analysis results for polymers prepared according to this procedure.

TABLE 5

| Example | Mp | Mn | Mw | Mz | PDI |
|---|---|---|---|---|---|
| 2.1 | 9488 | 6971 | 9895 | 13379 | 1.42 |
| 2.2 | 9298 | 6906 | 9810 | 13305 | 1.42 |

Variation of Temperature

The effects of temperature on polymer synthesis were also studied. GPC analysis of the product polymers are described in Table 6.

TABLE 6

| Example | Mp | Mn | Mw | Mz | PDI |
|---|---|---|---|---|---|
| T = 80° C. | | | | | |
| 2.3 | 5355 | 5124 | 6361 | 8004 | 1.24 |
| 2.4 | 5355 | 5076 | 6307 | 7933 | 1.24 |
| T = 110° C. | | | | | |
| 2.5 | 8896 | 6931 | 9857 | 13470 | 1.42 |
| 2.6 | 8896 | 6936 | 9800 | 13300 | 1.41 |
| T = 140° C. | | | | | |
| 2.7 | 1983 | 907 | 1676 | 2836 | 1.85 |
| 2.8 | 2118 | 1120 | 1961 | 3196 | 1.75 |
| T = 165° C. | | | | | |
| 2.9 | 555 | 507 | 530 | 555 | 1.05 |
| 2.10 | 523 | 485 | 506 | 527 | 1.04 |

Example 3. Deprotection of PCMMA-Boc

A3 solution of PCMMA-BOC (250 mg) in anhydrous dichloromethane (2.5 mL) and trifluoroacetic acid (2.5 mL) was stirred at room temperature for one hour. The reaction mixture was concentrated under reduced pressure. The residue was dried under high vacuum to give 245 mg of crude PCMMA. The crude copolymer was dissolved in anhydrous dichloromethane (1.5 mL) and dropped into diethyl ether (60 mL). The precipitate was washed with diethyl ether (60 mL) and dried under high vacuum to give 171 mg of Target PCMMA as off-white foam. GPC characterization data is provided in Table 7.

TABLE 7

| Example | Mp | Mn | Mw | Mz | PDI |
|---|---|---|---|---|---|
| 3.1 | 6829 | 5115 | 7285 | 9913 | 1.42 |

Example 4. Precipitation of PCMMA Polymers

Polyester polymers prepared herein (e.g., polymers prepared according to Example 3) can be precipitated from solvents following synthesis. Precipitation of stereochemically enriched polymers are described below.

Precipitation of (RS) PCMMA-TFA

An (R,S)-PCMMA cationic polymer comprising trifluoroacetate (TFA) counterions was prepared and then precipitated as shown in Scheme 4 and Table 8. Table 8 also includes characterization data for the polymers obtained following precipitation.

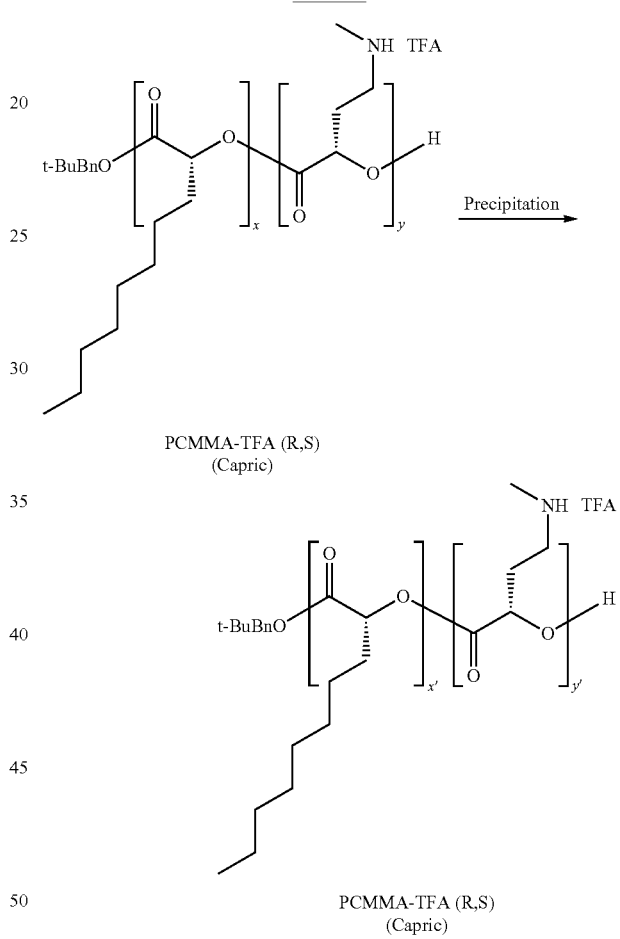

Scheme 4

TABLE 8

| No. | SAMPLE DETAIL | Mp | Mn | Mw | Mz | PDI |
|---|---|---|---|---|---|---|
| 4.1 | PCMMA-TFA (RS) (Et$_2$O/CH$_2$Cl$_2$; 1$^{st}$ Precipitation) | 2663 | 2150 | 2832 | 3677 | 1.32 |
| 4.2 | PCMMA-TFA (RS) (Et$_2$O/CH$_2$Cl$_2$ 2$^{nd}$ Precipitation) | 2688 | 2165 | 2818 | 3605 | 1.32 |
| 4.3 | PCMMA-TFA (RS) (Et$_2$O/CH$_2$Cl$_2$ 3$^{rd}$ Precipitation) | 2589 | 2142 | 2777 | 3556 | 1.3 |
| 4.4 | PCMMA-TFA (RS) (Et$_2$O/CH$_2$Cl$_2$ mother liquor) | 873 | 1008 | 1097 | 1201 | 1.09 |

An (S,S)-PCMMA cationic polymer comprising trifluoroacetate (TFA) counterions was prepared and then precipitated as shown in Scheme 5 and Table 9. Table 9 also includes characterization data for the polymers obtained following precipitation.

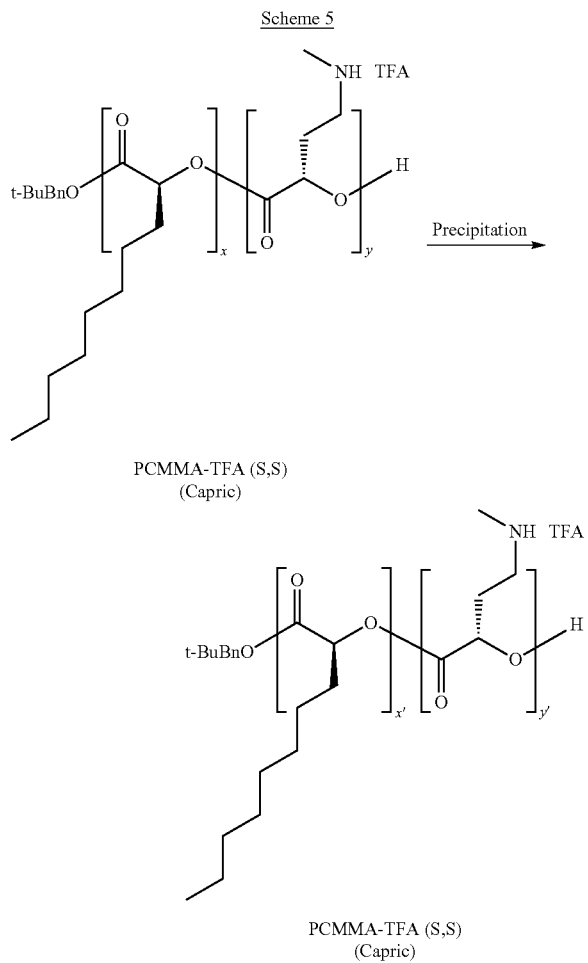

TABLE 9

| No. | SAMPLE DETAIL | Mp | Mn | Mw | Mz | PDI |
|---|---|---|---|---|---|---|
| 4.5 | PCMMA-TFA (SS) (Et$_2$O/CH$_2$Cl$_2$; 1$^{st}$ Precipitation) | 8323 | 5461 | 8211 | 11243 | 1.5 |
| 4.6 | PCMMA-TFA (SS) (Et$_2$O/CH$_2$Cl$_2$ 2$^{nd}$ Precipitation) | 8323 | 5292 | 7866 | 10578 | 1.49 |
| 4.7 | PCMMA-TFA (SS) (Et$_2$O/CH$_2$Cl$_2$ 3$^{rd}$ Precipitation) | 7181 | 4927 | 7125 | 9574 | 1.45 |
| 4.8 | PCMMA-TFA (RS) (Et$_2$O/CH$_2$Cl$_2$ mother liquor) | 865 | 1172 | 1425 | 1798 | 1.22 |

Example 5. Administration of PCMMA and mRNA Compositions to Animal Subjects

This example illustrates that polymer/mRNA compositions disclosed herein are useful in effectively delivering mRNA to one or more target cells, causing these cells to express encoded protein.

mRNA

Codon-optimized firefly luciferase messenger RNA (FFLuc mRNA) was synthesized by in vitro transcription from a plasmid DNA template encoding the gene. Following in vitro transcription, a 5' cap structure (Cap 1) (Fechter, P. et al., J. Gen. Virology (2005) 86:1239-1249) and a 3' poly(A) tail of approximately 445 nucleotides were added. The 5' and 3' untranslated regions present in the FFLuc mRNA are represented as X (SEQ ID NO: 2) and Y (SEQ ID NO: 3), respectively, in SEQ ID NO: 1, as indicated below.

(SEQ ID NO. 1)
XATGGAAGATGCCAAAAACATTAAGAAGGGCCCAGCGCCATTCTACCCAC

TCGAAGACGGGACCGCCGGCGAGCAGCTGCACAAAGCCATGAAGCGCTAC

GCCCTGGTGCCCGGCACCATCGCCTTTACCGACGCACATATCGAGGTGGA

CATTACCTACGCCGAGTACTTCGAGATGAGCGTTCGGCTGGCAGAAGCTA

TGAAGCGCTATGGGCTGAATACAAACCATCGGATCGTGGTGTGCAGCGAG

AATAGCTTGCAGTTCTTCATGCCCGTGTTGGGTGCCCTGTTCATCGGTGT

GGCTGTGGCCCCAGCTAACGACATCTACAACGAGCGCGAGCTGCTGAACA

GCATGGGCATCAGCCAGCCCACCGTCGTATTCGTGAGCAAGAAAGGGCTG

CAAAAGATCCTCAACGTGCAAAAGAAGCTACCGATCATACAAAAGATCAT

CATCATGGATAGCAAGACCGACTACCAGGGCTTCCAAAGCATGTACACCT

TCGTGACTTCCCATTTGCCACCCGGCTTCAACGAGTACGACTTCGTGCCC

GAGAGCTTCGACCGGGACAAAACCATCGCCCTGATCATGAACAGTAGTGG

CAGTACCGGATTGCCCAAGGGCGTAGCCCTACCGCACCGCACCGCTTGTG

TCCGATTCAGTCATGCCCGCGACCCCATCTTCGGCAACCAGATCATCCCC

GACACCGCTATCCTCAGCGTGGTGCCATTTCACCACGGCTTCGGCATGTT

CACCACGCTGGGCTACTTGATCTGCGGCTTTCGGGTCGTGCTCATGTACC

GCTTCGAGGAGGAGCTATTCTTGCGCAGCTTGCAAGACTATAAGATTCAA

TCTGCCCTGCTGGTGCCCACACTATTTAGCTTCTTCGCTAAGAGCACTCT

CATCGACAAGTACGACCTAAGCAACTTGCACGAGATCGCCAGCGGCGGGG

CGCCGCTCAGCAAGGAGGTAGGTGAGGCCGTGGCCAAACGCTTCCACCTA

CCAGGCATCCGCCAGGGCTACGGCCTGACAGAAACAACCAGCGCCATTCT

GATCACCCCCGAAGGGGACGACAAGCCTGGCGCAGTAGGCAAGGTGGTGC

CCTTCTTCGAGGCTAAGGTGGTGGACTTGGACACCGGTAAGACACTGGGT

GTGAACCAGCGCGGCGAGCTGTGCGTCCGTGGCCCCATGATCATGAGCGG

CTACGTTAACAACCCCGAGGCTACAAACGCTCTCATCGACAAGGACGGCT

GGCTGCACAGCGGCGACATCGCCTACTGGGACGAGGACGAGCACTTCTTC

ATCGTGGACCGGCTGAAGAGCCTGATCAAATACAAGGGCTACCAGGTAGC

CCCAGCCGAACTGGAGAGCATCCTGCTGCAACACCCCAACATCTTCGACG

CCGGGGTCGCCGGCCTGCCCGACGACGATGCCGGCGAGCTGCCCGCCGCA

GTCGTCGTGCTGGAACACGGTAAAACCATGACCGAGAAGGAGATCGTGGA

CTATGTGGCCAGCCAGGTTACAACCGCCAAGAAGCTGCGCGGTGGTGTTG

TGTTCGTGGACGAGGTGCCTAAAGGACTGACCGGCAAGTTGGACGCCCGC

AAGATCCGCGAGATTCTCATTAAGGCCAAGAAGGGCGGCAAGATCGCCGT

GTAAY

```
                                                 (SEQ ID NO. 2)
X (5' UTR Sequence) =

ATTTAGGTGACACTATAGGACAGATCGCCTGGAGACGCCATCCACGCTGT

TTTGACCTCCATAGAAGACACCGGGACCGATCCAGCCTCCGCGGCCGGGA
``` pared by mixing each with 1 mg/ml FFLuc mRNA (in water) at a 1:1 (v:v) ratio to a predetermined dose volume as indicated in Table 11.

For IV administration, PCMMA (S,S) polymer or PCMMA (S,S) polymer/DMG-PEG:FFLuc mRNA complexes were prepared by mixing each with 0.4 mg/ml FFLuc mRNA (in water) at 1:1 (v:v) ratio to predetermined dose volume (Table 11).

TABLE 11

| Group No. | No. of Animals | Test Article | Dose Levels | Conc. (ug/ul) | Dose Volume (per animal) | Dosing Regimen | Terminal Time Point |
|---|---|---|---|---|---|---|---|
| 1 | 3 | PCMMA (S,S) | 25 ug/animal | 0.5 | 50 ul | Once on Day 1 via IM injection (quadriceps) | At 24 hours after administration |
| 2 | 3 | PCMMA (S,S)/ DMG-PEG | 25 ug/animal | 0.5 | | | |
| 3 | 3 | PCMMA (S,S) | 5 mg/kg | 0.5 | 10 ml/kg | Once on Day 1 via Sc injection | |
| 4 | 3 | PCMMA (S,S)/ DMG-PEG | 5 mg/kg | 0.5 | | | |
| 5 | 3 | PCMMA (S,S) | 1 mg/kg | 0.2 | 5 ml/kg | Once on Day 1 via IV injection | |
| 6 | 3 | PCMMA (S,S)/ DMG-PEG | 1 mg/kg | 0.2 | | | |
| 7 | 3 | NT* | N/A | N/A | N/A | N/A | On Day 2 |

*N/T-Non-treatment control;
N/A-not applicable;
IM-Intramuscular;
SC-Subcutaneous;
IV-intravenous

```
                      -continued
ACGGTGCATTGGAACGCGGATTCCCCGTGCCAAGAGTGACTCACCGTCCT TGACACG
                                                 (SEQ ID NO. 3)
Y (3' UTR Sequence) =

CGGGTGGCATCCCTGTGACCCCTCCCCAGTGCCTCTCCTGGCCCTGGAAG

TTGCCACTCCAGTGCCCACCAGCCTTGTCCTAATAAAATTAAGTTGCATC
```

Polymer and Polymer/Lipid Formulations Used for Dosing

PCMMA polymers were formulated with or without DMG-PEG as set forth in Table 10 below.

TABLE 10

| Polymer | Concentration (mg/ml) | DMG-PEG (mg/ml) |
|---|---|---|
| N/P 10 | 100% or 93% | 0% or 7% |
| PCMMA (S,S) | 12.92 | 0 |
| PCMMA (S,S)/ DMG-PEG | 12.92 | 5.8 |

For IM and SC administration, PCMMA (S,S) polymer or PCMMA (S,S) polymer/DMG-PEG formulations were prepared by dissolving in water to reach the concentrations shown in Table 10. The N/P ratio was maintained at 10 for all formulations. PCMMA (S,S) polymer or PCMMA (S,S) polymer/DMG-PEG:FFLuc mRNA complexes were pre- The studies were performed using male CD-1 mice, which were approximately 7-9 weeks of age. Six groups of mice (each n=3) were dosed via a single intramuscular injection into the quadriceps muscle (IM), subcutaneous injection into the loose skin over the interscapular region (SC) or intravenous injection through the tail vein (IV). One animal was used as a non-treatment control in this study. Mice were euthanized at 24 hours post dose administration. The non-treatment control animal was euthanized on Day 2. All animals were euthanized by $CO_2$ asphyxiation followed by thoracotomy and exsanguination. The collected blood was discarded, and all animals were perfused with saline by cardiac perfusion. Following perfusion, liver, spleen, heart, both lungs, both quadriceps, both kidneys and brachial, axillary and inguinal lymph nodes were collected. Whole animal imaging was performed by IVIS imaging at 24 hours post dose administration. Organs were imaged by IVIS imaging and organs were placed for imaging.

Imaging Results

Whole Animal

Animals dosed intramuscularly with PCMMA (S,S) polymer/DMG-PEG:FFLuc mRNA complexes showed detectable FFLuc protein expression at the site of administration. In contrast, animals dosed with the complexes subcutaneously or intravenously showed little or no FFLuc protein expression (Table 12).

Organs

With respect to the various organs harvested, FFLuc protein was detected in the quadriceps muscle after treatment 24 hours post IM administration. Further, FFLuc protein was detected in the spleen after treatment 24 hours post IV administration. There was no detectable FFLuc protein in any organs of animals dosed SC with PCMMA (S,S) polymer/DMG-PEG:FFLuc mRNA complexes (Table 12).

TABLE 12

| Group No. | No. of Animals | Test Article | Dosing Method | Result |
|---|---|---|---|---|
| 1 | 3 | PCMMA (S,S) | IM | no expression |
| 2 | 3 | PCMMA (S,S)/ DMG-PEG | IM | FFLuc protein expressed in spleen |
| 3 | 3 | PCMMA (S,S) | SC | no expression |
| 4 | 3 | PCMMA (S,S)/ DMG-PEG | SC | no expression |
| 5 | 3 | PCMMA (S,S) | IV | FFLuc protein expressed in spleen |
| 6 | 3 | PCMMA (S,S)/ DMG-PEG | IV | no expression |
| 7 | 3 | N/A | N/T | no expression |

*N/T-Non-treatment control;
N/A-not applicable;
IM-Intramuscular;
SC-Subcutaneous;
IV-intravenous While a number of embodiments of this invention have been described, it is apparent that the basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

What is claimed is:

1. A pharmaceutical composition comprising:

a polymer comprising monomers having the following structure:

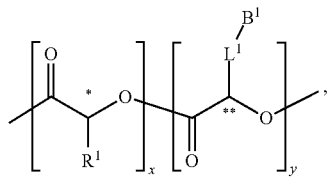

wherein $R^1$ is $C_6$-$C_{20}$ alkyl, $C_6$-$C_{20}$ alkenyl, or $C_6$-$C_{20}$ alkynyl;

$L^1$ is $C_2$-$C_{20}$ alkylene;

$B^1$ is $NR^2R^3$ or a 5- to 10-membered heteroaryl group;

$R^2$ is hydrogen or $C_1$-$C_{20}$ alkyl;

$R^3$ is hydrogen, $C_1$-$C_{20}$ alkyl, or an N-protecting group;

or $R^2$ and $R^3$, together with the nitrogen to which they are attached, combine to form a 5- to 10-membered heterocyclic group;

x is an integer of 5 to 500; and y is an integer of 5 to 500; and one or more polynucleotides.

2. The pharmaceutical composition of claim 1, comprising the polymer wherein x=y.

3. The pharmaceutical composition of claim 2, where said polymer comprises the repeating unit:

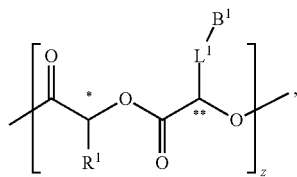

wherein z is an integer of 5 to 500.

4. The pharmaceutical composition of claim 3, wherein the polymer has the following structure:

wherein $R^4$ and $R^5$ are each independently hydrogen, $C_1$-$C_{12}$ alkyl, or $C_7$-$C_{12}$ alkaryl.

5. The pharmaceutical composition of claim 1, comprising the polymer wherein $R^1$ is unsubstituted $C_6$-$C_{14}$ alkyl or unsubstituted $C_6$-$C_{10}$ alkyl.

6. The pharmaceutical composition of claim 1, comprising the polymer wherein $B^1$ is a 5 to 10-membered heteroaryl group.

7. The pharmaceutical composition of claim 1, comprising the polymer wherein $B^1$ is $NR^2R^3$.

8. The pharmaceutical composition of claim 7, comprising the polymer wherein:

$R^2$ is independently hydrogen or $C_1$-$C_{20}$ alkyl; and $R^3$ is independently hydrogen, $C_1$-$C_{20}$ alkyl, or an N-protecting group.

9. The pharmaceutical composition of claim 8, comprising the polymer wherein:

$R^2$ is hydrogen;

and/or $R^3$ is unsubstituted $C_1$-$C_6$ alkyl or —C(O)O(CH$_3$)$_3$.

10. The pharmaceutical composition of claim 1, comprising the polymer wherein L1 is independently unsubstituted $C_2$-$C_{10}$ alkylene.

11. The polymer of any one of claim 1, comprising the polymer wherein L1 is —CH$_2$CH$_2$—.

12. The pharmaceutical composition of claim 1 where said polymer comprises the following monomers:

13. The pharmaceutical composition of claim 1, where said polymer comprises the following monomers:

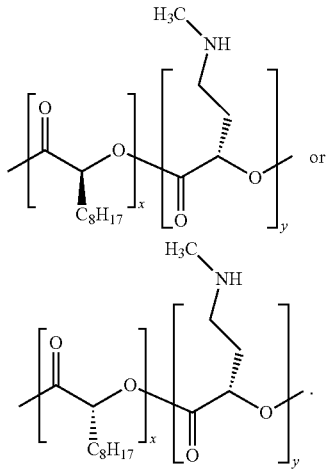 or

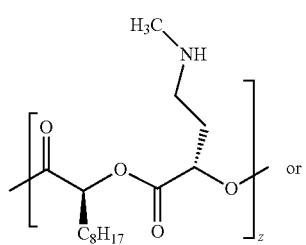

14. The pharmaceutical composition of claim 3, where said polymer comprises repeating units that are:

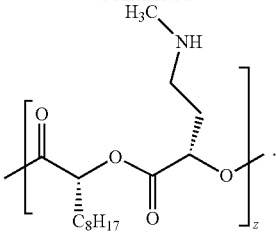 or

-continued

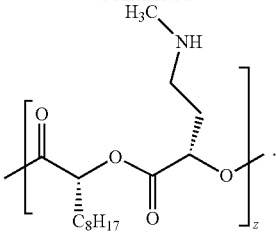

15. The pharmaceutical composition of claim 12, where said polymer comprises an end group $R^4$ that is attached to an —O-moiety, and an end group —$OR^5$ that is attached to a carbonyl moiety, wherein $R^4$ is hydrogen, and $R^5$ is —$CH_2C_6H_4{}^tBu$.

16. The pharmaceutical composition of claim 1, further comprising one or more cationic lipids, one or more non-cationic lipids, one or more cholesterol-based lipids and one or more PEG-modified lipids.

17. The pharmaceutical composition of claim 16, comprising up to about 15% of total PEG-modified lipids.

18. The pharmaceutical composition of claim 1, wherein one or more polynucleotides comprise mRNA.

19. The pharmaceutical composition of claim 18, wherein the mRNA encodes an enzyme, an antibody, or an antigen.

20. A method of treating a disease in a subject, comprising administering to the subject an effective amount of the pharmaceutical composition of claim 1.

* * * * *

SEQUENCE LISTING

```
Sequence total quantity: 3
SEQ ID NO: 1            moltype = DNA  length = 1910
FEATURE                 Location/Qualifiers
misc_feature            1..1910
                        note = source = /note="Description of Artificial Sequence:
                        Synthetic polynucleotide"
source                  1..1910
                        mol_type = other DNA
                        organism = synthetic construct
SEQUENCE: 1
atttaggtga cactatagga cagatcgcct ggagacgcca tccacgctgt tttgacctcc   60
atagaagaca ccgggaccga tccagcctcc gcggccggga acggtgcatt ggaacgcgga  120
ttccccgtgc caagagtgac tcaccgtcct tgacacgatg gaagatgcca aaaacattaa  180
gaagggccca gcgccattct acccactcga agacgggacc gccggcgagc agctgcacaa  240
agccatgaag cgctacgccc tggtgcccgg caccatcgcc tttaccgacg cacatatcga  300
ggtggacatt acctacgccg agtacttcga gatgagcgtt cggctggcag aagctatgaa  360
gcgctatggg ctgaatacaa accatcggat cgtggtgtgc agcgagaata gcttgcagtt  420
cttcatgccc gtgttgggtg ccctgttcat cggtgtggct gtggcccccag ctaacgacat  480
ctacaacgag cgcgagctgc tgaacagcat gggcatcagc cagcccaccg tcgtattcgt  540
gagcaagaaa gggctgcaaa agatcctcaa cgtgcaaaag aagctaccga tcatacaaaa  600
gatcatcatc atggatagca agaccgacta ccagggcttc caaagcatgt acaccttcgt  660
gacttcccat ttgccacccg gcttcaacga gtacgacttc gtgcccgaga gcttcgaccg  720
ggacaaaacc atcgccctga tcatgaacag tagtggcagt accggattgc ccaagggcgt  780
agccctaccg caccgcaccg cttgtgtccg attcagtcat gcccgcgacc ccatcttcgg  840
caaccagatc atccccgaca ccgctatcct cagcgtggtg ccatttcacc acggcttcgg  900
catgttcacc acgctgggct acttgatctg cggctttcgg gtcgtgctca tgtaccgctt  960
cgaggaggag ctattcttgc gcagcttgca agactataag attcaatctg ccctgctggt 1020
gcccacacta tttagcttct tcgctaagag cactctcatc gacaagtacg acctaagcaa 1080
cttgcacgag atcgccagcg gcggggcgcc gctcagcaag gaggtaggtg aggccgtggc 1140
caaacgcttc cacctaccag gcatccgcca gggctacggc ctgacagaaa caaccagcgc 1200
cattctgatc accccgaag gggacgacaa gcctggcgca gtaggcaagg tggtgccctt 1260
cttcgaggct aaggtggtgg acttggacac cggtaagaca ctgggtgtga accagcgcgg 1320
cgagctgtgc gtccgtggcc ccatgatcat gagcggctac gttaacaacc ccgaggctac 1380
aaacgctctc atcgacaagg acggctggct gcacagcggc gacatcgcct actgggacga 1440
ggacgagcac ttcttcatcg tggaccggct gaagagccgt atcaaataca agggctacca 1500
ggtagcccca gccgaactgg agagcatcct gctgcaacac cccaacatct tcgacgccgg 1560
ggtcgccggc ctgcccgacg acgatgccgg cgagctgccc gccgcagtcg tcgtgctgga 1620
acacggtaaa accatgaccg agaaggagat cgtggactat gtggccagcc aggttacaac 1680
cgccaagaag ctgcgcggtg gtgttgtgtt cgtggacgag gtgcctaaag gactgaccgg 1740
caagttggac gcccgcaaga tccgcgagat tctcattaag gccaagaagg gcggcaagat 1800
cgccgtgtaa cgggtggcat ccctgtgacc cctcccagt gcctctcctg gccctggaag 1860
ttgccactcc agtgcccacc agccttgtcc taataaaatt aagttgcatc                1910

SEQ ID NO: 2            moltype = DNA  length = 157
FEATURE                 Location/Qualifiers
misc_feature            1..157
                        note = source = /note="Description of Artificial Sequence:
                        Synthetic polynucleotide"
source                  1..157
                        mol_type = other DNA
```

```
                organism = synthetic construct
SEQUENCE: 2
atttaggtga cactatagga cagatcgcct ggagacgcca tccacgctgt tttgacctcc    60
atagaagaca ccgggaccga tccagcctcc gcggccggga acggtgcatt ggaacgcgga   120
ttccccgtgc caagagtgac tcaccgtcct tgacacg                            157

SEQ ID NO: 3            moltype = DNA   length = 100
FEATURE                 Location/Qualifiers
misc_feature            1..100
                        note = source = /note="Description of Artificial Sequence:
                        Synthetic polynucleotide"
source                  1..100
                        mol_type = other DNA
                        organism = synthetic construct
SEQUENCE: 3
cgggtggcat ccctgtgacc cctccccagt gcctctcctg gccctggaag ttgccactcc    60
agtgcccacc agccttgtcc taataaaatt aagttgcatc                         100
```